US00RE48587E

(19) United States
(12) Reissued Patent
Gu

(10) Patent Number: US RE48,587 E
(45) Date of Reissued Patent: Jun. 8, 2021

(54) ULTRASONIC PROBE APPARATUS AND ULTRASONIC IMAGING APPARATUS USING THE SAME

(71) Applicant: SAMSUNG MEDISON CO., LTD., Gangwon-do (KR)

(72) Inventor: Jin Ho Gu, Seongnam-si (KR)

(73) Assignee: SAMSUNG MEDISON CO., LTD., Gangwon-do (KR)

(21) Appl. No.: 16/528,968

(22) Filed: Aug. 1, 2019

Related U.S. Patent Documents

Reissue of:
(64) Patent No.: 9,746,448
Issued: Aug. 29, 2017
Appl. No.: 14/684,019
Filed: Apr. 10, 2015

(30) Foreign Application Priority Data

Dec. 26, 2014 (KR) ..... 10-2014-0190566

(51) Int. Cl.
*G01N 29/24* (2006.01)
*G01N 29/28* (2006.01)
(Continued)

(52) U.S. Cl.
CPC ..... *G01N 29/28* (2013.01); *B06B 1/0622* (2013.01); *G01N 29/24* (2013.01); *G10K 11/002* (2013.01);
(Continued)

(58) Field of Classification Search
CPC ..... A61B 8/44; A61B 8/4444; A61B 8/546; A61B 8/4494; G01N 29/28; G01N 29/34;
(Continued)

(56) References Cited

U.S. PATENT DOCUMENTS 4,424,465 A * 1/1984 Ohigashi ..... B06B 1/0622 310/335
4,917,097 A * 4/1990 Proudian ..... A61B 8/12 600/463
(Continued)

OTHER PUBLICATIONS

European Communication dated Jan. 27, 2020 issued in European Patent Application No. 15174040.4.
(Continued)

*Primary Examiner* — Robert L Nasser
(74) *Attorney, Agent, or Firm* — Morgan, Lewis & Bockius LLP

(57) ABSTRACT

An ultrasonic probe apparatus and an ultrasonic imaging apparatus are disclosed. The ultrasonic probe apparatus includes: an ultrasonic transducer configured to output an electrical signal upon receiving ultrasonic waves; a sound absorption unit, one surface of which is an installation surface of the ultrasonic transducer and is electrically connected to the ultrasonic transducer; a first electronic circuit electrically connected to the sound absorption unit; and a substrate connection unit disposed between the sound absorption unit and the first electronic circuit, configured to electrically interconnect the first electronic circuit and the sound absorption unit. The ultrasonic imaging apparatus includes the above ultrasonic probe and a main body.

34 Claims, 41 Drawing Sheets

(51) Int. Cl.
*B06B 1/06* (2006.01)
*G10K 11/00* (2006.01)
*A61B 8/00* (2006.01)

(52) U.S. Cl.
CPC ..... *A61B 8/4444* (2013.01); *A61B 8/4494* (2013.01); *G01N 2291/0289* (2013.01); *G01N 2291/269* (2013.01)

(58) Field of Classification Search
CPC ..... G01N 2291/0289; G01N 2291/269; G01N 29/2437; B06B 1/0622; B06B 1/0633; G01K 11/002; G01K 11/004
See application file for complete search history.

(56) References Cited

U.S. PATENT DOCUMENTS 6,625,854 B1 9/2003 Sudol et al.
2004/0100163 A1 5/2004 Baumgartner et al.
2005/0146247 A1* 7/2005 Fisher ..... G01N 29/2406 310/334
2006/0150380 A1 7/2006 Ossmann
2006/0184035 A1* 8/2006 Kimura ..... A61B 8/12 600/466
2006/0232164 A1* 10/2006 Kondo ..... G10K 11/02 310/322
2008/0134793 A1 6/2008 Woychik et al.
2008/0139945 A1* 6/2008 Hu ..... A61B 8/00 600/459
2008/0183078 A1* 7/2008 Haider ..... A61B 1/0005 600/443
2008/0200812 A1 8/2008 Osawa
2008/0238262 A1* 10/2008 Takeuchi ..... B06B 1/0622 310/346
2008/0242989 A1* 10/2008 Koide ..... A61B 8/0833 600/443
2009/0030325 A1* 1/2009 Hyuga ..... A61B 1/05 600/459
2009/0034370 A1* 2/2009 Guo ..... B06B 1/0622 367/180
2009/0062656 A1* 3/2009 Hyuga ..... A61B 8/4488 600/459
2010/0013358 A1* 1/2010 Nakayama ..... B06B 1/0633 310/348
2010/0324425 A1* 12/2010 Kim ..... G10K 11/004 600/459
2011/0074244 A1* 3/2011 Osawa ..... A61B 8/00 310/318
2011/0114303 A1* 5/2011 Rhim ..... A61B 8/00 165/185
2011/0257532 A1* 10/2011 Sasaki ..... G01S 7/521 600/459
2011/0295124 A1 12/2011 Shikata et al.
2013/0145611 A1 6/2013 Guo
2013/0286593 A1* 10/2013 Cho ..... G01N 29/326 361/707
2013/0301395 A1* 11/2013 Hebrard ..... G01S 7/52079 367/189
2013/0315035 A1* 11/2013 Tai ..... B06B 1/0622 367/140
2014/0033822 A1* 2/2014 Yoon ..... G01H 9/00 73/643
2014/0249419 A1* 9/2014 Morita ..... A61B 8/4444 600/459
2014/0323865 A1* 10/2014 Hoppmann ..... A61B 8/14 600/443
2015/0099960 A1* 4/2015 Ryu ..... A61B 8/4483 600/407
2015/0157292 A1* 6/2015 Gu ..... A61B 8/4444 600/459
2015/0164473 A1* 6/2015 Kim ..... G01S 15/8997 600/443
2015/0265244 A1* 9/2015 Park ..... A61B 8/12 600/462
2015/0320393 A1* 11/2015 Kim ..... A61B 8/546 600/459
2016/0007964 A1* 1/2016 Ona ..... G01S 15/8927 600/459
2016/0066885 A1* 3/2016 Jin ..... A61B 8/4444 600/459
2016/0143618 A1* 5/2016 Park ..... G01N 29/226 600/459
2016/0228088 A1* 8/2016 Okuno ..... H04R 1/06
2016/0282455 A1* 9/2016 Scarsella ..... G01S 7/5208

OTHER PUBLICATIONS

Chinese Office Action dated Mar. 10, 2020 issued in Chinese Patent Application No. 201510706654.0 (with English translation).
Extended European Search Report issued in European Application No. 15174040.4 dated Jul. 4, 2016.

* cited by examiner

ULTRASONIC PROBE APPARATUS AND ULTRASONIC IMAGING APPARATUS USING THE SAME

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATION

This application claims the benefit of Korean Patent Application No. 10-2014-0190566, filed on Dec. 26, 2014 in the Korean Intellectual Property Office, the disclosure of which is incorporated herein by reference.

BACKGROUND

1. Field

Examplary embodiments relate to an ultrasonic probe apparatus and an ultrasonic imaging apparatus.

2. Description of the Related Art

An imaging apparatus captures an image of an object using visible light, infrared light, radiation, ultrasonic waves, microwaves, or Free Induction Decay (FID) signals derived from a magnetic resonance phenomenon, and generates an internal or external image of the object. Examples of the imaging apparatus may include a camera, an infrared camera, a radiation imaging apparatus, an ultrasonic imaging apparatus, etc.

The ultrasonic imaging apparatus obtains images by capturing an internal image of the object using ultrasonic waves, and displays the obtained images for user recognition. The ultrasonic imaging apparatus directly irradiates ultrasonic waves to a target site contained in the object, collects the ultrasonic waves reflected from the target site, and thus generates an ultrasound image using the collected ultrasonic waves. The ultrasonic imaging apparatus may collect ultrasonic waves generated from a target site contained in the object using laser beams or the like, and may thus generate an ultrasound image using the collected ultrasonic waves.

The ultrasonic imaging apparatus may irradiate ultrasonic waves to the inside of the object using an ultrasonic probe or may receive ultrasonic waves from the inside of the object using the ultrasonic probe. There are various kinds of ultrasonic probes according to categories of objects and categories of the image-captured parts of the objects or according to categories of target sites contained in the objects.

SUMMARY

Therefore, it is an aspect of the present invention to so provide an ultrasonic probe apparatus and an ultrasonic imaging apparatus, which can efficiently absorb ultrasonic waves emitted in a direction opposite to an object using ultrasonic elements.

Additional aspects of the invention will be set forth in part in the description which follows and, in part, will be obvious from the description, or may be learned by practice of the invention.

In accordance with one aspect of the present invention, an ultrasonic probe apparatus includes: an ultrasonic transducer configured to output an electrical signal upon receiving ultrasonic waves; a sound absorption unit, one surface of which is an installation surface of the ultrasonic transducer and is electrically connected to the ultrasonic transducer; a first electronic circuit electrically connected to the sound absorption unit; and a substrate connection unit disposed between the sound absorption unit and the first electronic circuit, configured to electrically interconnect the first electronic circuit and the sound absorption unit.

The substrate connection unit may include a second electronic circuit configured to electrically interconnect the first electronic circuit and the sound absorption unit.

The second electronic circuit may include a substrate connection unit electrically connected to the first electronic circuit.

The substrate connection unit may include a first substrate connection unit configured to electrically interconnect the sound absorption unit and the first electronic circuit.

The first substrate connection unit may be electrically connected to the ultrasonic transducer.

The sound absorption unit may include at least one first connection unit electrically connected to the ultrasonic transducer, wherein the first substrate connection unit contacts the first connection unit.

The second electronic circuit may include at least one output unit configured to output a signal processed by the first electronic circuit, wherein the substrate connection unit includes a second substrate connection unit configured to electrically interconnect the first electronic circuit and the at least one output unit.

The substrate connection unit may include: a first opening configured to pass through a range from one surface to the other surface of the second electronic circuit; and a conductor installed at an inner lateral surface of the first opening and electrically coupled to the first electronic circuit.

The conductor may be configured to shield the first opening.

The substrate connection unit may further include a second opening formed to pass through the conductor.

The substrate connection unit may further include a filling material configured to shield the second opening.

The conductor may be deposited on an inner lateral surface of the first opening.

The conductor may be installed at one surface of the second electronic circuit located in a vicinity of the first opening.

The second electronic circuit may include a rigid flexible printed circuit board (PCB).

The second electronic circuit may include at least one of a first region that is not curved and a second region that is flexibly curved.

The second electronic circuit may include a substrate connection unit that is electrically connected to the first electronic circuit and is formed in the first region.

A second connection unit (a bump) may be mounted to the first electronic circuit, wherein the second connection unit is attached to the substrate connection unit of the second electronic circuit.

The ultrasonic probe may further include: a separation unit disposed between the second electronic circuit and the first electronic circuit, and formed of a nonconductive material that prevents the second electronic circuit from directly contacting the first electronic circuit.

The second connection unit may be mounted to the first electronic circuit so as to pass through the separation unit.

The ultrasonic probe apparatus may further include: a heat conduction unit mounted to the other surface of the first electronic circuit, and to perform heat transmission of the first electronic circuit.

The sound absorption unit may include: a sound absorption material for absorbing sound; and a first connection unit configured to pass through the sound absorption material so as to electrically interconnect the ultrasonic transducer and the first electronic circuit.

At least one first connection unit may be mounted to a single ultrasonic transducer.

The ultrasonic probe may further include: an acoustic enhancer disposed between the ultrasonic transducer and the sound absorption unit, and configured to amplify the electrical signal generated from the ultrasonic transducer.

The sound absorption unit may be formed of a sound absorption material formed to absorb sound waves or ultrasonic waves.

A seating surface at which the ultrasonic transducer or an acoustic enhancer seated may be formed at one surface of the sound absorption unit, wherein the acoustic enhancer is coupled to the ultrasonic transducer so as to amplify the electrical signal generated from the ultrasonic transducer.

The first electronic circuit may include a processor configured to focus signals generated from the ultrasonic transducer.

The first electronic circuit may include at least one application specific integrated circuit (ASIC).

In accordance with another aspect of the present invention, an ultrasonic imaging apparatus includes: an ultrasonic probe configured to receive ultrasonic waves; and a main body configured to control operations of the ultrasonic probe, and to perform image processing of an ultrasound image corresponding to the received ultrasonic waves. The ultrasonic probe includes: an ultrasonic transducer configured to output an electrical signal upon receiving the ultrasonic waves; a sound absorption unit, one surface of which is an installation surface of the ultrasonic transducer and is electrically connected to the ultrasonic transducer; a first electronic circuit electrically connected to the sound absorption unit; and a substrate connection unit disposed between the sound absorption unit and the first electronic circuit, configured to electrically interconnect the first electronic circuit and the sound absorption unit.

The substrate connection unit may include a second electronic circuit configured to electrically interconnect the first electronic circuit and the sound absorption unit.

The second electronic circuit may include a substrate connection unit electrically connected to the first electronic circuit.

The substrate connection unit may include a first substrate connection unit configured to electrically interconnect the sound absorption unit and the first electronic circuit.

The first substrate connection unit may be electrically connected to the ultrasonic transducer.

The sound absorption unit may include at least one first connection unit electrically connected to the ultrasonic transducer, wherein the first substrate connection unit contacts the first connection unit.

The second electronic circuit may include at least one output unit configured to output a signal processed by the first electronic circuit, wherein the substrate connection unit includes a second substrate connection unit configured to electrically interconnect the first electronic circuit and the at least one output unit.

The second electronic circuit may include a rigid flexible printed circuit board (PCB).

The second electronic circuit may include at least one of a first region that is not curved and a second region that is flexibly curved.

The second electronic circuit may include a substrate connection unit that is electrically connected to the first electronic circuit and is formed in the first region.

A second connection unit may be mounted to the first electronic circuit. The second connection unit may be attached to the substrate connection unit of the second electronic circuit.

The ultrasonic imaging apparatus may further include: a separation unit disposed between the second electronic circuit and the first electronic circuit, and formed of a nonconductive material that prevents the second electronic circuit from directly contacting the first electronic circuit.

The second connection unit may be mounted to the first electronic circuit so as to pass through the separation unit.

The ultrasonic imaging apparatus may further include: a heat conduction unit mounted to the other surface of the first electronic circuit, and to perform heat transmission of the first electronic circuit.

The sound absorption unit may include: a sound absorption material for absorbing sound; and a first connection unit configured to pass through the sound absorption material so as to electrically interconnect the ultrasonic transducer and the first electronic circuit.

At least one first connection unit may be mounted to a single ultrasonic transducer.

The ultrasonic imaging apparatus may further include: an acoustic enhancer disposed between the ultrasonic transducer and the sound absorption unit, and configured to amplify the electrical signal generated from the ultrasonic transducer.

The sound absorption unit may be formed of a sound absorption material configured to absorb sound waves or ultrasonic waves.

A seating surface at which the ultrasonic transducer or an acoustic enhancer seated may be formed at one surface of the sound absorption unit, wherein the acoustic enhancer is coupled to the ultrasonic transducer so as to amplify the electrical signal generated from the ultrasonic transducer.

The first electronic circuit may include a processor configured to focus signals generated from the ultrasonic transducer.

The first electronic circuit may include at least one application specific integrated circuit (ASIC).

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Figure 1:
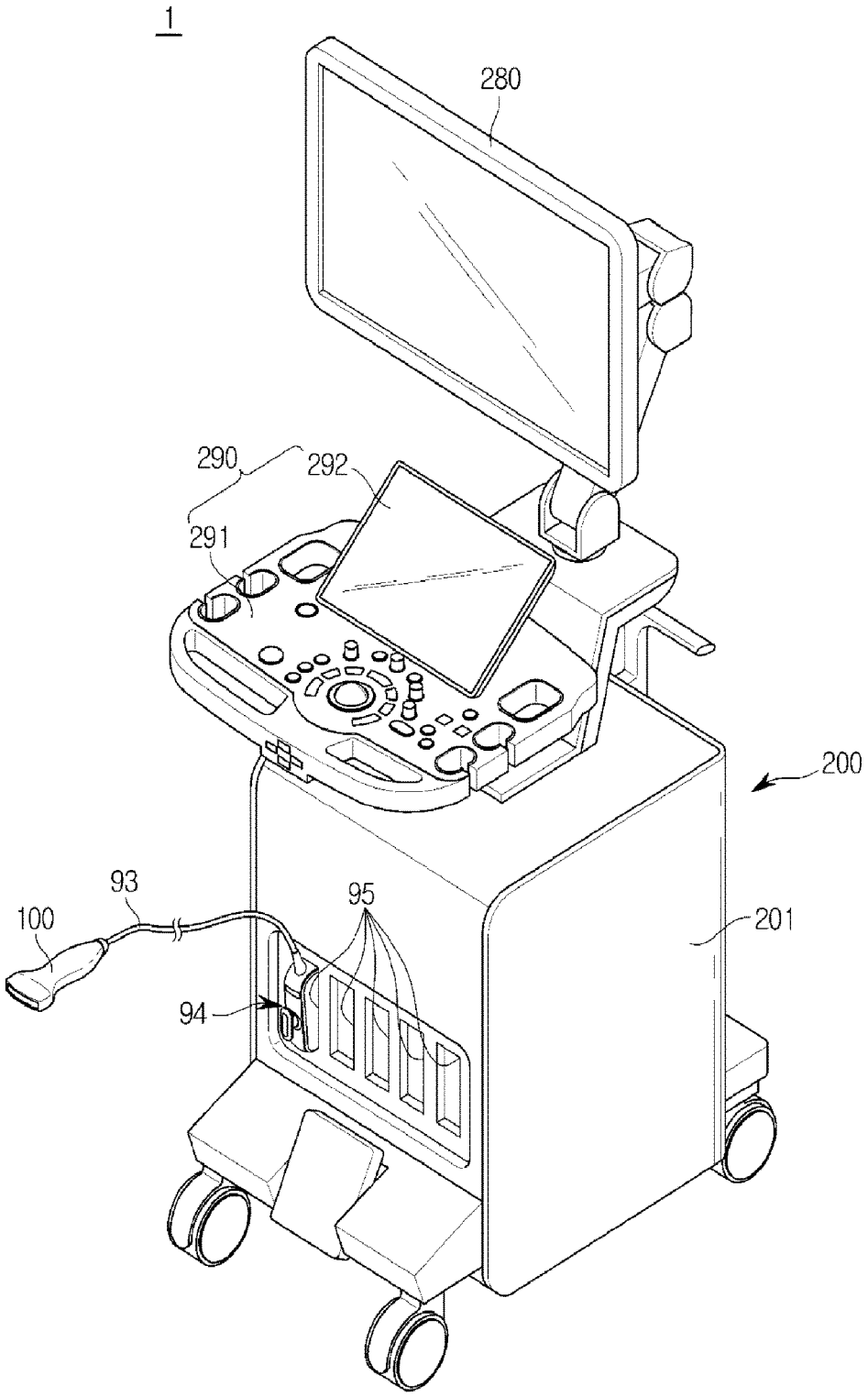
FIG. 1 is a perspective view illustrating an ultrasonic imaging apparatus according to an embodiment of the present invention.

Reference will now be made in detail to the embodiments of the present invention, examples of which are illustrated in the accompanying drawings, wherein like reference numerals refer to like elements throughout.

Figure 2A:
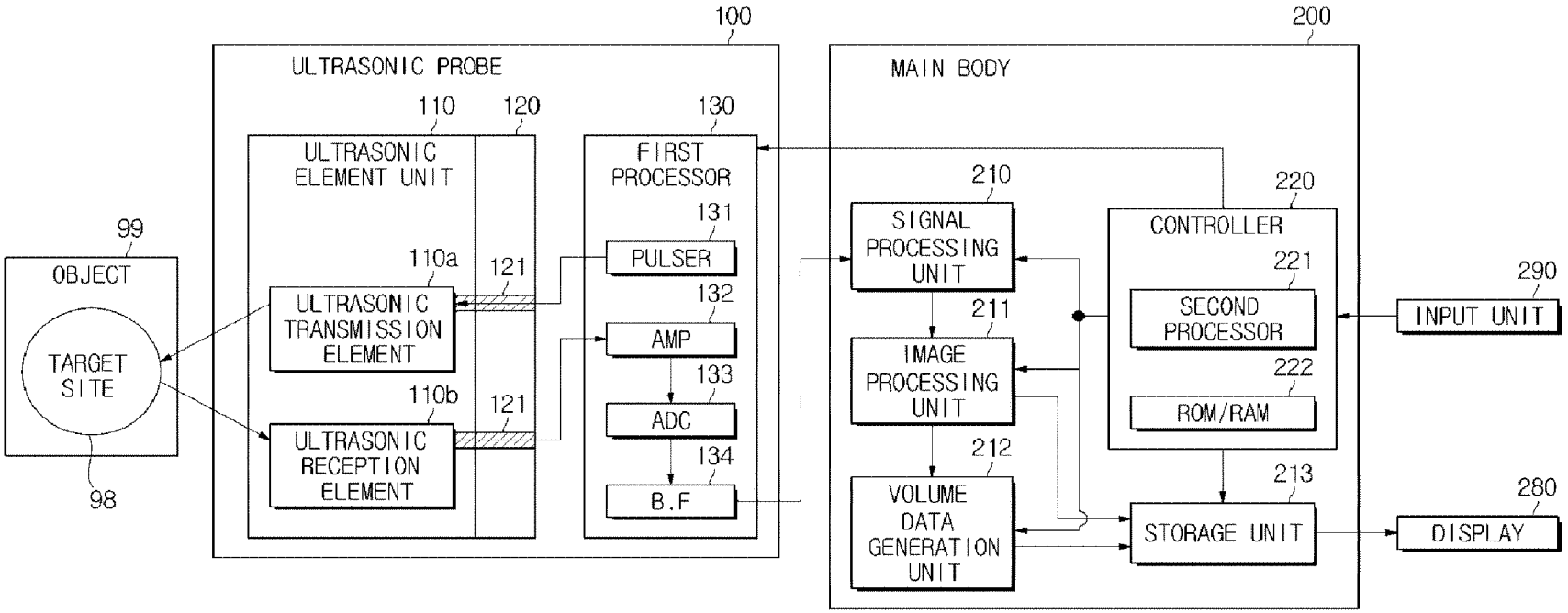
FIG. 2A is a block diagram illustrating an ultrasonic imaging apparatus according to an embodiment of the present invention.

FIG. 1 is a perspective view illustrating an ultrasonic imaging apparatus according to an embodiment of the present invention. FIG. 2A is a block diagram illustrating an ultrasonic imaging apparatus according to an embodiment of the present invention.

Referring to FIGS. 1 and 2A, the ultrasonic imaging apparatus 1 may include an ultrasonic probe 100 and a main body 200.

The ultrasonic probe 100 may collect ultrasonic waves, and may transmit an electrical signal corresponding to the collected ultrasonic waves to the main body 200. In accordance with the embodiment, the ultrasonic probe 100 may perform beamforming of ultrasonic waves of the collected channels, and may also transmit the beamformed signals to the main body 200.

The main body 200 may control overall operations of the ultrasonic imaging apparatus 1. In addition, the main body 200 may generate an ultrasound image such as a B-mode image by performing either beamforming or image processing using electrical signals received from the ultrasonic probe 100, and may display the generated ultrasound image on the display unit 280 for user recognition. In addition, various electronic components for controlling overall operations of either the ultrasonic probe 100 or the main body 200 may be contained in the main body 200. The main body 200 may receive various commands from the user who uses an input unit 290, generate a control signal corresponding to the user command, and thus control the ultrasonic imaging apparatus 1.

The ultrasonic probe 100 may transmit/receive data to/from the main body 200 through a cable 93 or a wireless communication module.

In accordance with one embodiment, the ultrasonic probe 100 and the main body 200 may communicate with each other using the connection cable 93 shown in FIG. 1. The electrical signal generated from the ultrasonic probe 100 may be transmitted to the main body 200 through the connection cable 93. In addition, a control command generated from the main body 200 may also be transmitted to the ultrasonic probe 100 through the connection cable 93.

A connector 94 may be provided at one end of the connection cable 93. The connector 94 may be detachably coupled to the port 95 provided at the external frame 201 of the main body 200. If the connector 94 is coupled to the port 95, the ultrasonic probe 100 and the main body 200 may be interconnected to communicate with each other. In the meantime, according to one embodiment, the ultrasonic probe 100 may be fixed to the other end of the connection cable 93. That is, the ultrasonic probe 100 and the connection cable may be integrated. In accordance with another embodiment, the connector (not shown) capable of being coupled to or detached from the port contained in the ultrasonic probe 100 may also be provided at the other end of the connection cable 93.

In accordance with another embodiment, the ultrasonic probe 100 and the main body 200 may transmit electrical signals generated from the ultrasonic probe 100 to the main body 200 over a wireless communication network or may also transmit the electrical signal generated from the main body 200 to the ultrasonic probe 100. In this case, a wireless communication module including an antenna and a wireless communication chip may be installed in each of the ultrasonic probe and the main body 200. The wireless communication module may be a short-range wireless communication module based on various short-range communication technologies, for example, Bluetooth, Bluetooth low energy, infrared data association (IrDA), Wireless Fidelity (Wi-Fi), Wi-Fi Direct, Ultra Wideband (UWB), Near Field Communication (NFC), etc. Alternatively, the wireless communication module may be a mobile communication module supporting 3GPP, 3GPP2 or IEEE wireless communication networks defined by the International Telecommunication Union (ITU).

The ultrasonic probe 100 will hereinafter be described in detail.

The ultrasonic probe 100 may receive ultrasonic waves generated from the object, and may convert the received ultrasonic waves into an electrical signal. For convenience of description and better understanding of the present invention, the electrical signal obtained by conversion of the received ultrasonic waves will hereinafter be referred to as an ultrasonic signal.

The ultrasonic probe 100 may include an ultrasonic element unit 110 for generating or receiving ultrasonic waves; and a first processor 130. The first processor 130 may be electrically connected to the ultrasonic element unit 110, may control operations of the ultrasonic element unit 110, or may perform signal processing using the electrical signal generated from the ultrasonic element unit.

The ultrasonic element unit 110 may include an ultrasonic transducer for generating ultrasonic waves or generating an electrical signal corresponding to the ultrasonic waves. The ultrasonic transducer may convert AC (Alternating Current) energy having a predetermined frequency into mechanical vibration having the same frequency, may generate ultrasonic waves, or may convert mechanical vibration having a predetermined frequency based on ultrasound into AC energy. Therefore, the ultrasonic transducer may generate ultrasonic waves or may output electrical signals corresponding to the received ultrasonic waves. In more detail, upon receiving AC power from a battery or the like, a piezoelectric vibrator or a thin film of the ultrasonic transducer vibrates according to the AC power, such that a plurality of ultrasonic waves is generated.

Here, the ultrasonic transducer may be one of, for example, a magnetostrictive ultrasonic transducer using the magnetostrictive effect of a magnetic body, a piezoelectric ultrasonic transducer using the piezoelectric effect of a piezoelectric material, and a capacitive micromachined ultrasonic transducer (cMUT) transmitting/receiving ultrasonic waves using vibration of hundreds or thousands of micromachined thin films. Further, the ultrasonic transducer may be one of other kinds of transducers which may generate ultrasonic waves according to an electrical signal or generate an electrical signal according to ultrasonic waves.

Referring to FIG. 2A, the ultrasonic element unit 110 may include an ultrasonic transmission element 110a and an ultrasonic reception element 110b. The ultrasonic transmission element 110a may generate ultrasonic waves having a frequency corresponding to a frequency of a pulse signal according to a pulse signal received from the first processor 130 or the second processor 220. The generated ultrasonic waves may be irradiated to a target site 98 of the object 99. The generated ultrasonic waves may be focused on at least one target site 98 contained in the object 99. In this case, the irradiated ultrasonic waves may be focused on a single target site 98 (i.e., single focusing), and may also be focused on a plurality of target sites 98 (i.e., multi-focusing).

The ultrasonic reception element 110b may receive ultrasonic waves reflected from the target site 98 or may receive ultrasonic waves generated from the target site 98 according to laser or the like, and may convert the received signals into an ultrasonic signal. The ultrasonic reception element 110b may include a plurality of ultrasonic transducers, each of which outputs an ultrasonic signal, so that the ultrasonic reception element 110b may output ultrasonic signals of a plurality of channels.

In accordance with the embodiment, the ultrasonic element unit 110 may include ultrasonic transmission/reception (Tx/Rx) elements (not shown) capable of generating and receiving ultrasonic waves. In this case, the ultrasonic transmission element 110a and the ultrasonic reception element 110b may be omitted as necessary.

The ultrasonic element unit 110 may be mounted to one surface of the sound absorption unit 120. A first connection unit 121 corresponding to each ultrasonic element unit 110 may be mounted to the sound absorption unit 120. In accordance with one embodiment, the first connection unit 121 may be mounted to the sound absorption unit 120 after passing through the sound absorption unit 120. In this case, the first connection unit 121 may be installed to pass through the range from one surface to the other surface of the sound absorption unit 120. In this case, one surface may indicate a surface to which the ultrasonic element unit 110 is mounted, and the other surface may indicate a surface to which the substrate connection unit (e.g., a second electronic circuit) is mounted. A detailed description of the sound absorption unit 120 and the first connection unit 121 will be given below.

The first processor 130 may generate and output the electrical signal for controlling the ultrasonic element unit 110, or may perform various kinds of signal processing using an ultrasonic signal received from the ultrasonic element unit 110.

The electrical signal generated from the first processor 130 may be transferred to the ultrasonic element unit 110 (e.g., the ultrasonic transmission element 110a) through the first connection unit 121. The ultrasonic transmission element 110a may be driven in response to the received electrical signal. In addition, the first processor 130 may receive the electrical signal corresponding to ultrasonic waves received by the ultrasonic element unit 110 (e.g., the ultrasonic reception element 110b) through the first connection unit 121.

The first processor 130 may be implemented by at least one semiconductor chip and associated electronic components. In accordance with the embodiment, the first processor 130 may also be implemented by at least one Application Specific Integrated Circuit (ASIC).

In accordance with the embodiment shown in FIG. 2A, the first processor 130 may include at least one of a pulser 131, an amplifier 132, an analog-to-digital converter (ADC) 133, and a beamformer 134.

The pulser 131 may generate a voltage having a predetermined frequency for driving the ultrasonic element unit 110, and may transmit the generated voltage to the ultrasonic element unit 110. The ultrasonic element unit 110 may be vibrated according to an amplitude and frequency of the output voltage of the pulser 131, and thus generate ultrasonic waves. The frequency and intensity of ultrasonic waves generated from the ultrasonic element unit 110 may be determined according to the amplitude and frequency of the voltage generated from the pulser 131. The output voltage of the pulser 131 may be applied to the ultrasonic element unit 110 at intervals of a predetermined time, so that ultrasonic waves generated from the ultrasonic element unit 110 may be focused on the target site 98 or may be steered in a specific direction.

In accordance with the embodiment, the pulser 131 may be mounted to the second processor 221. In this case, the first processor 130 may not include the pulser 131.

The amplifier (AMP) 132 may amplify ultrasonic signals generated from the ultrasonic reception element 110b of the ultrasonic element unit 110. A gain of the amplifier 132 may be arbitrarily determined by a system designer or a user. The amplifier 132 may differently amplify multi-channel ultrasonic signals generated from the plurality of ultrasonic element units 110 according to the embodiment, so that a difference in intensity between multi-channel ultrasonic signals can be compensated for.

If the amplified ultrasonic signals are analog signals, the ADC 132 may convert the analog signals into digital signals. The ADC 132 may perform sampling of ultrasonic signals acting as analog signals according to a predetermined sampling rate, so that it may output a digital signal.

A beamformer (B.F) 134 may focus ultrasonic signals input to a plurality of channels. The beamformer 134 may focus signals received from the ultrasonic element unit 110, the amplifier 132 or the ADC 133, and thus generate the beamformed signal. The beamformer 134 may perform various functions of multi-channel signals, for example, electronic beam scanning-, steering-, focusing-, apodizing-, and aperture-functions of multi-channel signals.

Figure 2B:
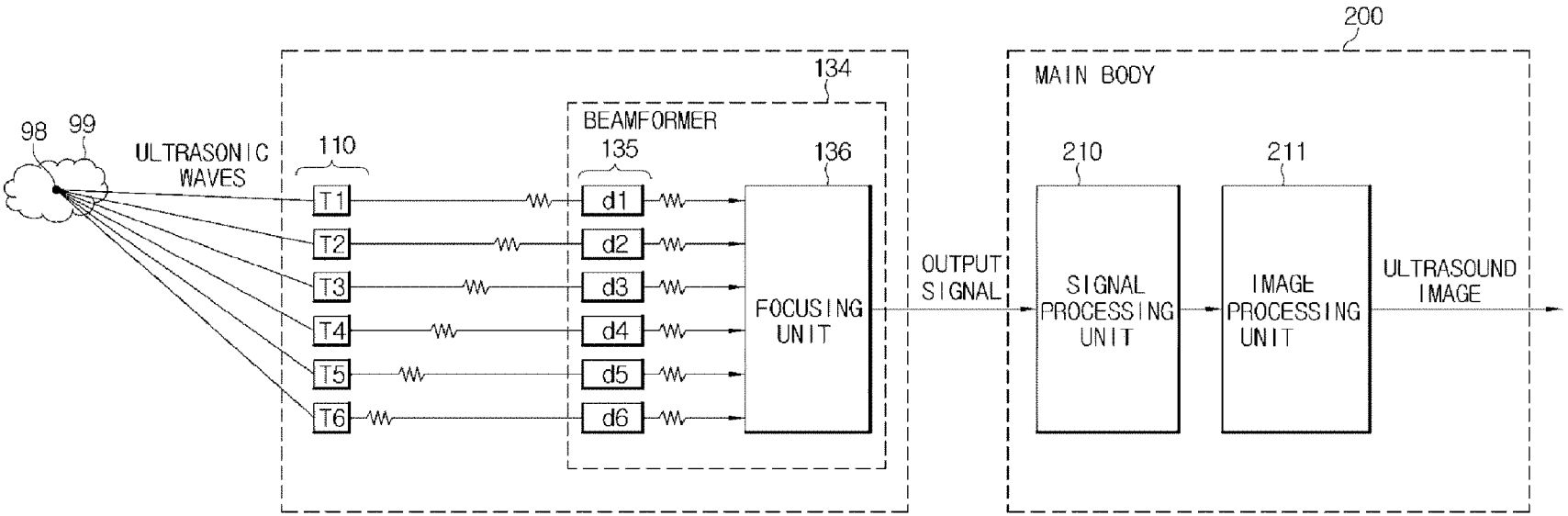
FIG. 2B is a conceptual diagram illustrating a beamforming process according to an embodiment of the present invention.

FIG. 2B is a conceptual diagram illustrating a beamforming process according to an embodiment of the present invention.

In accordance with the embodiment, the beamformer 134 may include a time-difference correction unit 135 and a receiver focusing unit 136 as shown in FIG. 2B.

The time-difference correction unit 135 may correct a time difference between multi-channel ultrasonic signals. There may arise a time difference between multi-channel ultrasonic signals generated from several ultrasonic element units 110 according to a distance from the target 98 to each ultrasonic element unit 110 or characteristics of the ultrasonic element unit 110. The time-difference correction unit 135 may delay transmission of some parts of multi-channel signals, so that it may correct a time difference between multi-channel signals. The time-difference correction unit 135 may be mounted to each channel of ultrasonic signals generated from the ultrasonic element unit 110.

The receiver focusing unit 136 may synthesize multi-channel ultrasonic signals, a time difference of which is corrected by the time-difference correction unit 135. The receiver focusing unit 136 may synthesize multi-channel ultrasonic signals by applying a predetermined weight to ultrasonic signals of respective channels. The predetermined weight may be determined irrespective of the ultrasonic signals, and may also be determined according to the ultrasonic signals. According to the synthesizing result of multi-channel ultrasonic signals, the receiver focusing unit 136 may output the beamformed signal. The beamformed signal may be transferred to the main body 200.

If the beamformer 134 is mounted to the first processor 130, it is necessary for the ultrasonic probe 100 to transmit only the beamformed signal to the main body 200. Accordingly, since the ultrasonic probe 100 need not transmit ultrasonic signals of all channels to the main body 200, system complexity can be reduced whereas system reliability can be increased.

The pulser 131, the amplifier 132, the ADC 133, and the beamformer 134 of the first processor 130 may be logically separated from each other. In this case, the first processor 130 may be implemented by one semiconductor chip and associated electronic components. In accordance with another embodiment, the pulser 131, the amplifier 132, and the ADC 133, and the beamformer 134 of the first processor 130 may also be physically separated from each other. If the pulser 131, the amplifier 132, and the ADC 133, and the beamformer 134 of the first processor 130 are physically separated from each other, each thereof may be implemented by one or at least two semiconductor chips and associated electronic components.

In accordance with the embodiment, at least one of the amplifier 132, the ADC 134, and the beamformer 134 of the first processor 130 may also be mounted to the main body 200. In this case, at least one of the amplifier 132, the ADC 134, and the beamformer 134 may be implemented by a Central Processing Unit (CPU) mounted to the main body 200 or a Graphics Processing Unit (GPU). If the amplifier 132, the ADC 134, and the beamformer 134 are mounted to the main body 200, signals generated from the ultrasonic element unit 110 may also be transferred to the main body 200 without conversion.

For example, the ultrasonic probe 100 may be a linear array probe, a convex array probe, or a sector phased array probe. In addition, the ultrasonic probe 100 may be a mechanical sector array probe.

A detailed internal structure of the ultrasonic probe 100 will hereinafter be described in detail.

The main body 200 will hereinafter be described with reference to FIG. 2A.

Referring to FIG. 2A, the main body 200 may include a signal processing unit 210, an image processing unit 211, a volume data generation unit 212, a storage unit 213, and a controller 220.

The signal processing unit 210 may perform signal processing of the beamformed signal in various ways. For example, the signal processor 210 may perform at least one of a filtering process, a detection process, and a compression process. The filtering process includes applying a filter to the beamformed signal so as to remove signals other than signals of a specific bandwidth. The filtering process may include a harmonic imaging process for removing a basic frequency component and passing harmonic signals. A detection process may convert a radio frequency (RF) format of a voltage of an ultrasonic signal into a video signal format. The compression process may reduce a difference in amplitude between ultrasonic signals. The signal processing unit 210 may be omitted as necessary.

The image processing unit 211 may convert the beamformed signal or signals processed by the signal processing unit 210 into an ultrasound image based on a still image or an ultrasound image based on a moving image. In addition, the image processing unit 211 may perform predetermined image processing of a still image or moving image.

The image processing unit 211 may generate an ultrasound image using scan conversion. The generated ultrasound image may include an A-mode ultrasound image, a B-mode ultrasound image, or an M-mode ultrasound image. The A-mode ultrasound image may indicate an ultrasound image obtained when reflection intensity is amplitude-imaged on the basis of the distance or time from the target site 98 to the ultrasonic probe 100. The B-mode ultrasound image may indicate an ultrasound image obtained when the ultrasonic intensity is represented using brightness. The M-mode ultrasound image may indicate an ultrasound image obtained when a variation of the operations of the object is imaged. The ultrasound image may include a Doppler image based on the Doppler effect.

The image processing unit 211 may correct the generated ultrasound image. For example, the image processing unit 211 may correct brightness, luminance, sharpness, contrast, or color of all or some regions of the ultrasound image in such a manner that a user can definitely view tissues contained in the ultrasound image. The image processing unit 211 may remove noise from the ultrasound image or may perform pixel interpolation of the ultrasound image.

The image processing unit 211 may transmit the generated or corrected ultrasound image to the storage unit 213 or may display the generated or corrected ultrasound image on the display unit 280. In addition, the image processing unit 211 may transmit the generated or corrected ultrasound image to the volume data generation unit 212, so that it can obtain ultrasonic volume data.

The volume data generation unit 212 may obtain ultrasonic volume data that indicates a three-dimensional (3D) volume using a two-dimensional (2D) ultrasound image generated or corrected by the image processing unit 211.

The signal processing unit 210, the image processing unit 211, or the volume data generation unit 212 may be implemented by a CPU or GPU. The CPU or GPU may be implemented by one or at least two semiconductor chips and associated electronic components.

The storage unit 213 may store various programs associated with functions of the controller 200, data, ultrasound images, and various kinds of information associated with the ultrasound images. The storage unit 213 may be implemented using a semiconductor storage unit, a magnetic disc storage unit, a magnetic tape storage unit, or the like.

The controller 220 may control overall operations of the ultrasonic imaging apparatus 1 according to a user command or a predefined configuration. For example, after the controller 220 generates a predetermined control command according to a frequency of ultrasonic waves to be irradiated, the controller 220 may transmit the generated control command to the pulser 131 of the first processor 130. The pulser 131 may apply a voltage having a predetermined frequency to the ultrasonic element unit 110 according to a control command. Accordingly, the ultrasonic element unit 110 may generate ultrasonic waves having a predetermined frequency, and thus apply the ultrasonic waves to the target site 98 of the object 99.

The controller 220 may include a second processor 221; and a storage unit 222, such as ROM or RAM, to assist the operations of the second processor 221. The second processor 221 may be implemented by a CPU. The CPU may be implemented by one or at least two semiconductor chips and associated electronic elements.

The display unit 280 may display an ultrasound image for user recognition. The display unit 280 may use a plasma display panel (PDP), a light emitting diode (LED), a liquid crystal display (LCD), or the like. The LED may include an organic light emitting diode (OLED). In addition, the display unit 280 may use a 3D display configured to represent a 3D image.

The input unit 290 may receive various commands related to control of the ultrasonic imaging apparatus 1 from the user. The input unit 290 may output an electrical signal in response to user manipulation, and may transmit the electrical signal to the second processor 220.

The input unit 290 may include a manipulation panel 291 to which various input devices are installed. For example, the input devices may include at least one of a keyboard, a mouse, a track ball, a knob, a touchpad, a paddle, various levers, a handle, a joystick, and various input devices.

The input unit 290 may include a touchscreen unit 292. The user may input various commands by touching a touch panel using a touch tool, such as a finger or a touch pen, of the touchscreen unit 292.

The touchscreen unit 292 may be implemented by a resistive touchscreen panel or a capacitive touchscreen panel. In addition, the touchscreen unit 292 may also use ultrasonic waves or infrared light.

The internal structure of the ultrasonic probe 100 will hereinafter be described in detail.

Figure 3:
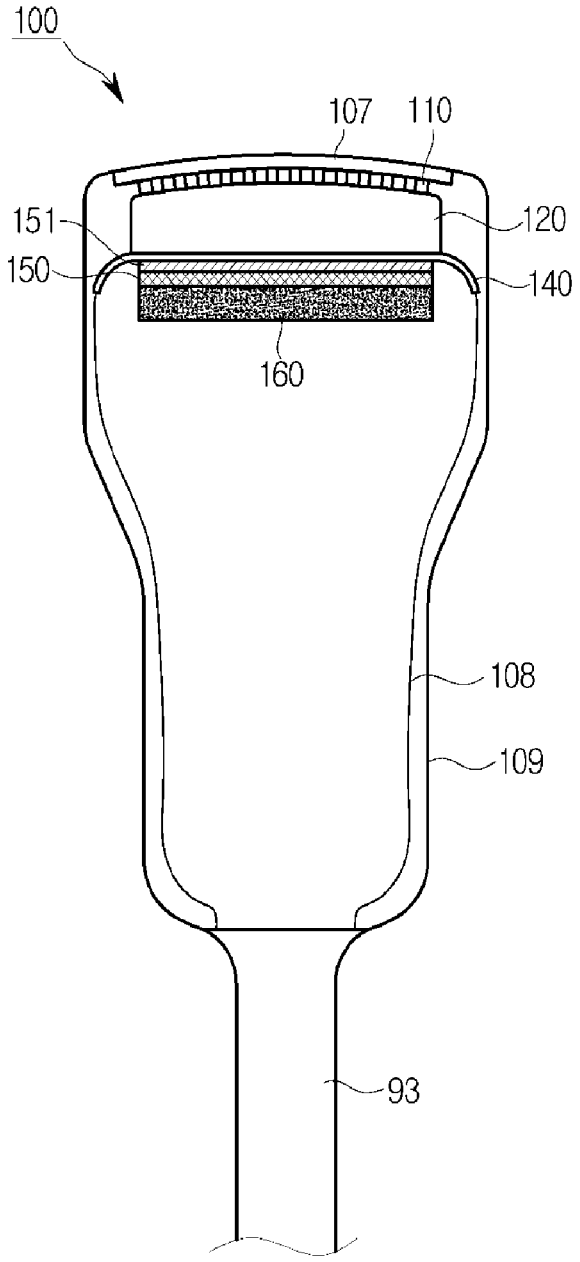
FIG. 3 illustrates the internal structure of an ultrasonic probe according to an embodiment of the present invention.
Figure 4:
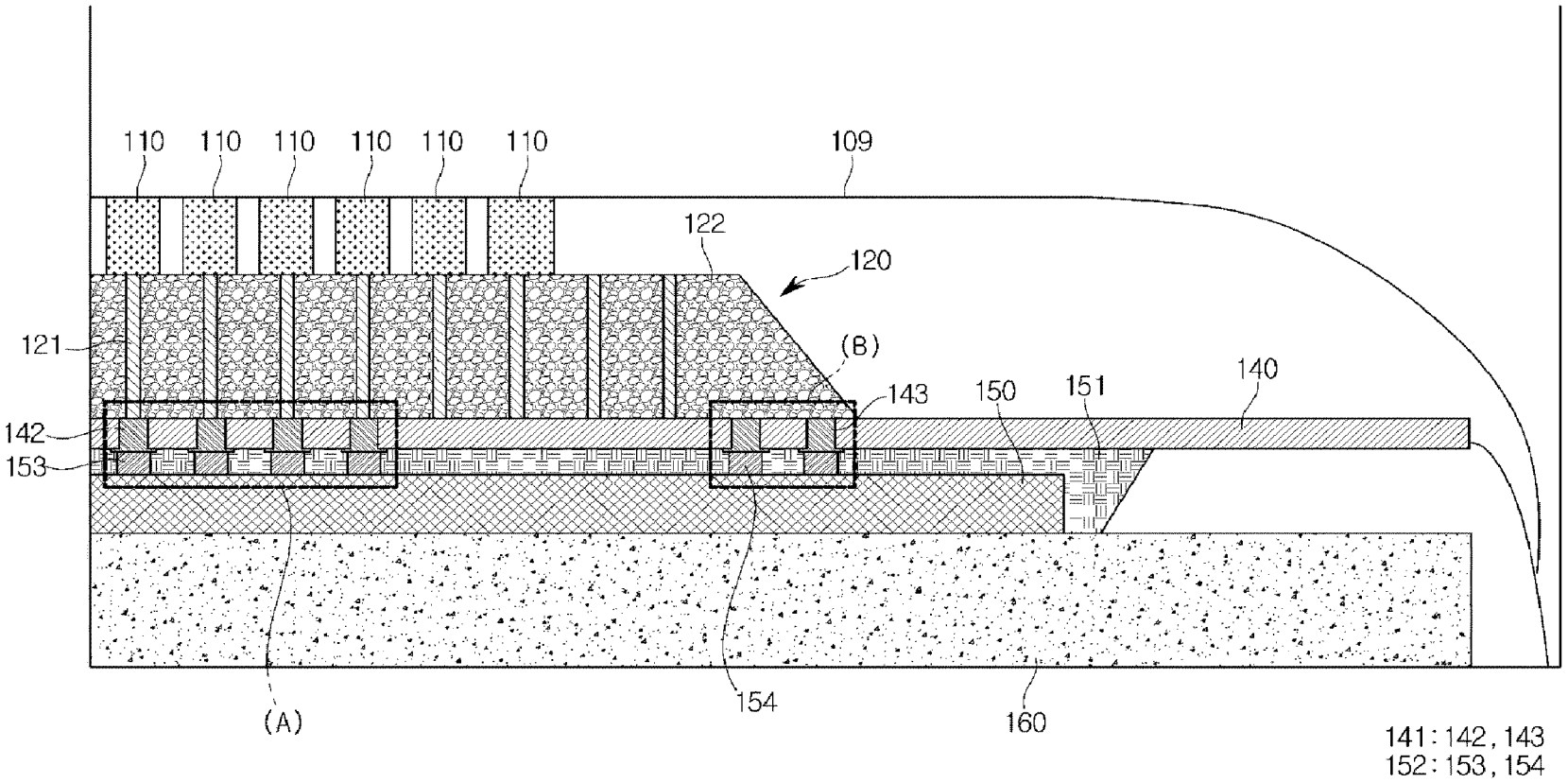
FIG. 4 is an exploded perspective view illustrating the internal structure of an ultrasonic probe according to a first embodiment of the present invention.

FIG. 3 illustrates the internal structure of an ultrasonic probe according to an embodiment of the present invention. FIG. 4 is an exploded perspective view illustrating the internal structure of an ultrasonic probe according to a first embodiment of the present invention.

Referring to FIGS. 3 and 4, the ultrasonic probe 100 may include an acoustic lens 109 installed at one end of the probe housing 107; an ultrasonic element unit 110 located close to the acoustic lens 109; a sound absorption unit 120, one surface of which contacts the ultrasonic element unit 110 seated therein; a second electronic circuit acting as a substrate connection unit installed at the other surface of the sound absorption unit 120; a first electrical circuit 150 electrically connected to the second electronic circuit and disposed at the other surface of the second electronic circuit 140; a heat conduction unit 160 configured to absorb heat generated from the first electronic circuit 150; and a conductive line (or a conductive wire) 108 configured to transmit the electrical signal generated from the first electronic circuit 150 to the main body 200.

The ultrasonic element unit 110, the sound absorption unit 120, the second electronic circuit 140, the first electronic circuit 150, the heat conduction unit 160, and the conductive line 180 may be installed in the probe housing 107. A cable 93 may be fixed to the other end of the probe housing 107 or may be detached from the other end of the probe housing 107.

The housing 107 may allow various electronic components of the ultrasonic probe 100 to be stably fixed, or may protect the electronic components from external impact. The housing 107 may be implemented by various metals or synthetic resins, and may be formed in various shapes according to a use purpose of the ultrasonic probe 100 or according to categories of objects or target sites.

The acoustic lens 109 may focus or emit sound waves or ultrasonic waves. The acoustic lens 109 may focus ultrasonic waves generated from the ultrasonic element unit 110 on the target site 98. The acoustic lens 109 may be formed of glass or synthetic fibers.

The ultrasonic element unit 110 may be mounted to one surface of the sound absorption unit 120. The ultrasonic element unit 110 may contact the acoustic lens 109 or may be disposed close to the acoustic lens 109.

Figure 5A:
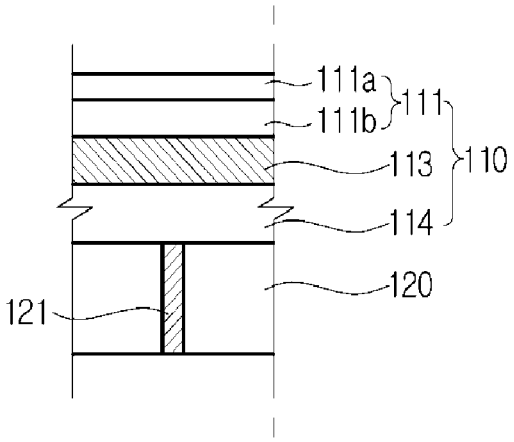
FIG. 5A is a conceptual diagram illustrating arrangement of an ultrasonic element unit according to a first embodiment of the present invention.

FIG. 5A is a conceptual diagram illustrating arrangement of an ultrasonic element unit according to a first embodiment of the present invention.

Referring to FIG. 5A, the ultrasonic element unit 110 may include a matching layer 111 capable of being implemented as one or at least two layers, an ultrasonic transducer 113, and an acoustic enhancer 114.

The matching layer 111 may maintain straightness or intensity of the ultrasonic waves generated from the ultrasonic transducer 113, or may minimize the problem in that the emitted ultrasonic waves do not reach the target site 98 and are reflected from a surface of the object 99 (e.g., the skin of a human being).

The matching layer 111 may include a plurality of matching layers, i.e., a first matching layer 111a and a second matching layer 111b. Each of the first matching layer 111a and the second matching layer 111b may be formed of a material having medium impedance between impedance of each transducer 113 and tissue impedance. If the matching layer 111 includes a plurality of matching layers (111a, 111b), the respective matching layers (111a, 111b) may contact each other.

One surface of the first matching layer 111a may contact the acoustic lens 109 or may be disposed close to the acoustic lens 109. The other surface of the first matching layer 111a may be attached to one surface of the second matching layer 111b. The ultrasonic transducer 113 may be attached to the other surface of the second matching layer 111b. In this case, one ultrasonic element unit 110 may also be attached to the other surface of the second matching layer 111b, and a plurality of ultrasonic element units may also be attached thereto.

In accordance with the embodiment, the acoustic matching layer 111 may include only one matching layer or may also include three or more matching layers.

As described above, the ultrasonic transducer 113 may convert the ultrasonic waves into electrical signals or vice versa. One surface of the ultrasonic transducer 113 may be attached to the second matching layer 111b.

The acoustic enhancer 114 may be attached to the other surface of the ultrasonic transducer 113. The acoustic enhancer 114 may amplify signals received from the first connection unit 121 so that the ultrasonic transducer 113 may generate the amplified ultrasonic waves. The ultrasonic transducer 113 may be attached to one surface of the acoustic enhancer 114. The other surface facing one surface of the acoustic enhancer 114 may contact the sound absorption unit 120 and the first connection unit 121. The acoustic enhancer 114 may be formed of a conductive material through which electricity flows.

Figure 5B:
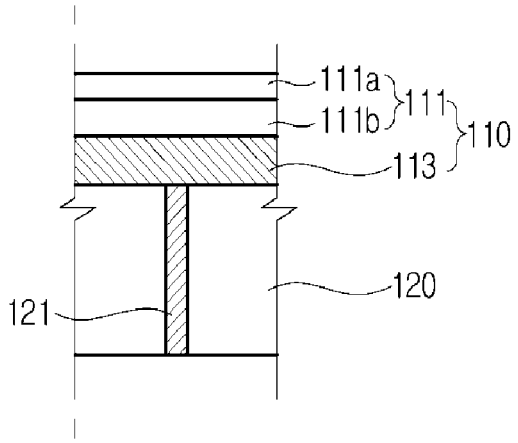
FIG. 5B is a conceptual diagram illustrating arrangement of an ultrasonic element unit according to a second embodiment of the present invention.

FIG. 5B is a conceptual diagram illustrating arrangement of an ultrasonic element unit according to a second embodiment of the present invention.

Referring to FIG. 5B, the acoustic enhancer 114 may be omitted, and only the matching layer 111 and the ultrasonic transducer 113 may be installed. In this case, the sound absorption unit 120 and the first connection unit 121 may be directly mounted to the ultrasonic transducer 113. The matching layer 111 and the ultrasonic transducer 113 are identical to those of FIG. 5A, and as such a detailed description thereof will herein be omitted for convenience of description.

Embodiments of the sound absorption unit 120 in which the ultrasonic element unit 110 is seated will hereinafter be described in detail.

Figure 6:
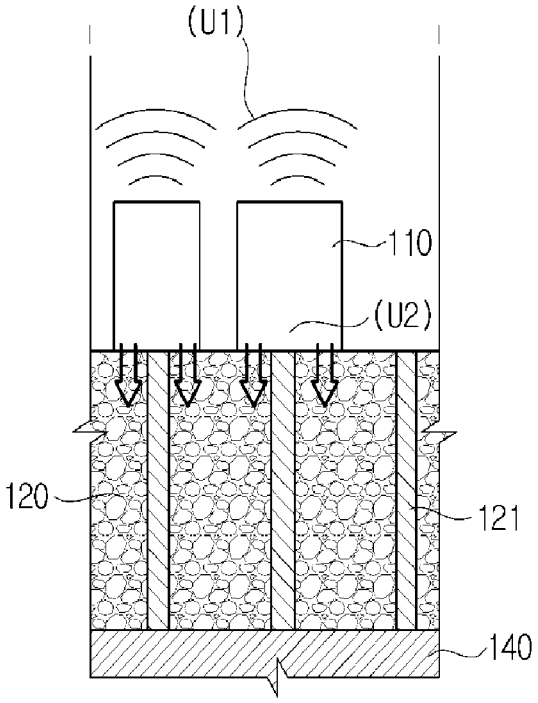
FIG. 6 is a conceptual diagram illustrating functions of a sound absorption unit.
Figure 7:
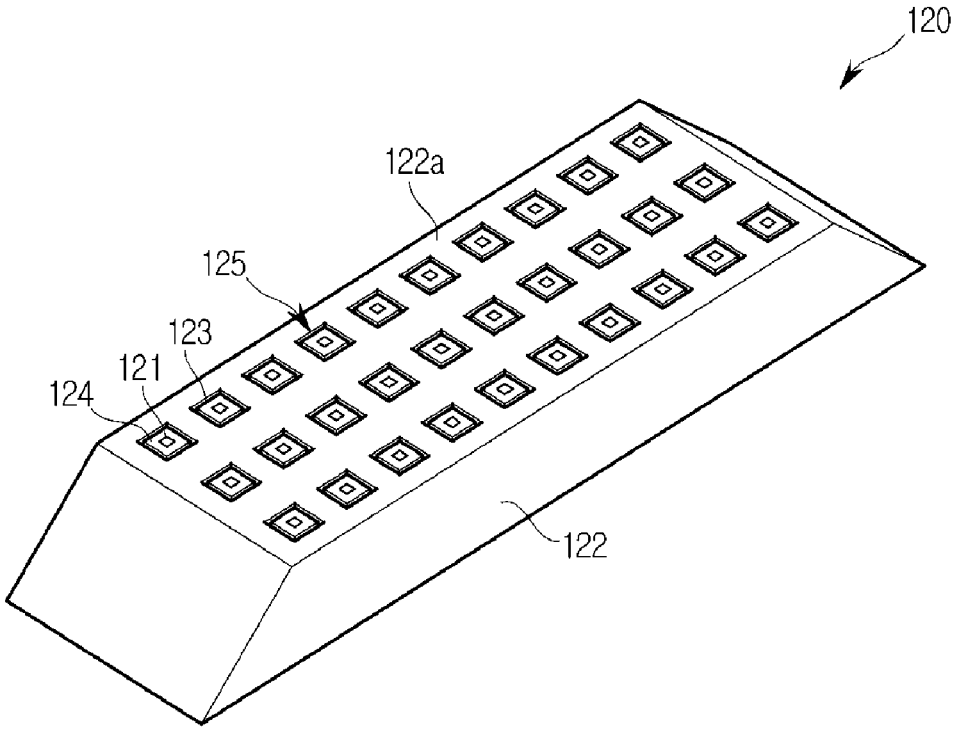
FIG. 7 is a perspective view illustrating a sound absorption unit according to a first embodiment of the present invention.
Figure 8:
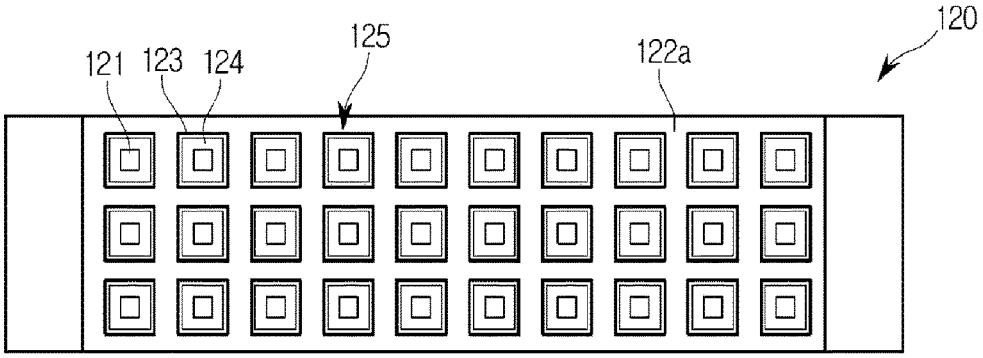
FIG. 8 is a plan view illustrating a sound absorption unit according to a first embodiment of the present invention.
Figure 9:
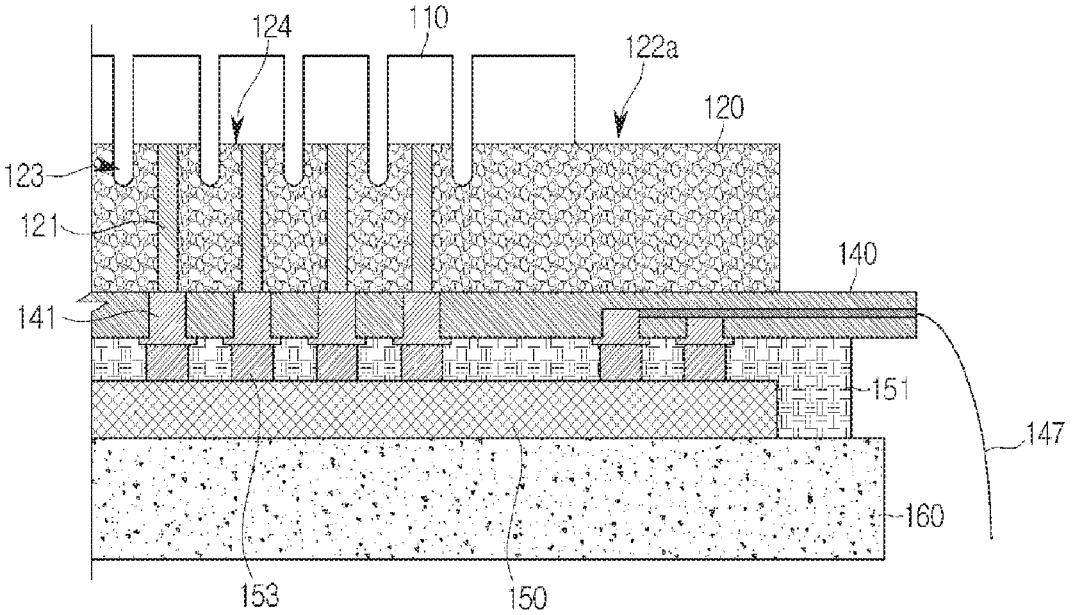
FIG. 9 is a lateral perspective view illustrating a sound absorption unit according to a first embodiment of the present invention.

FIG. 6 is a conceptual diagram illustrating functions of the sound absorption unit. FIG. 7 is a perspective view illustrating the sound absorption unit according to a first embodiment of the present invention. FIG. 8 is a plan view illustrating the sound absorption unit according to a first embodiment of the present invention. FIG. 9 is a lateral perspective view illustrating the sound absorption unit according to a first embodiment of the present invention.

As shown in FIG. 4, the ultrasonic element unit 110 may be attached to one surface of the sound absorption unit 120 according to the first embodiment, and the second electronic circuit 140 acting as the substrate connection unit may be attached to the other surface facing one surface.

Referring to FIG. 6, if the ultrasonic transducer 113 of the ultrasonic element unit 110 generates ultrasonic waves in response to a reception voltage, the generated ultrasonic waves may be emitted in the direction (u1) of the object, and may also be emitted in the direction (u2) of the sound absorption unit. As described above, the ultrasonic waves (u2) emitted in the direction of the sound absorption unit may cause noise in the ultrasound image. In order to prevent the occurrence of noise, the sound absorption unit 120 may be formed of a sound absorption material 122. The sound absorption material 122 may be a material capable of absorbing sound waves or ultrasonic waves. The sound absorption material 112 may absorb ultrasonic waves emitted in the direction from the ultrasonic transducer 113 to the sound absorption unit, and may reduce intensity of ultrasonic waves proceeding in an undesired direction. As a result, noise capable of being generated in the ultrasound image can be reduced.

The sound absorption material 122 of the sound absorption unit 120 may be formed of epoxy resin or a hafnium oxide material such as hafnium oxide metal powder. In addition, the sound absorption material 122 may be a mixture of epoxy resins, metals, and various synthetic resins. In addition, various materials capable of providing a function of absorbing sound waves or ultrasonic waves may be used as the sound absorption material 122.

In accordance with one embodiment, the sound absorption material 122 may be formed in a hexahedral shape as shown in FIGS. 7 to 9. The sound absorption material 122 may be formed in any of various columns or spheres. The external appearance of the sound absorption material 122 may be arbitrarily determined according to selection of a system designer.

Referring to FIGS. 4 to 9, at least one first connection unit 121 configured to pass through the range from one surface 122a to the other surface of the sound absorption material 122 may be mounted to the sound absorption material 122. Here, the other surface may be a surface facing one surface 122a of the sound absorption material 120. The first connection unit 121 may be provided to pass through the sound absorption material 122, so that the first connection unit 121 may be exposed to the outside at both of one surface 122a and the other surface of the sound absorption material 122.

The first connection unit 121 may be formed of a conductive material through which electricity flows. In this case, the conductive material may be any one of various metals through which electricity flows, for example, copper (Cu), gold (Au), or the like. Therefore, the first connection unit 121 may transmit an electrical signal generated from the ultrasonic element unit 110 to either the first electronic circuit 150 or the second electronic circuit 140, or may transmit an electrical signal generated from the first electronic circuit 150 or the second electronic circuit 140 to the ultrasonic element unit 110.

The first connection unit 121 may be formed in a hexahedral shape as shown in FIGS. 7 to 9. However, the shape of the first connection unit 121 is not limited thereto. In accordance with the embodiment, the first connection unit 121 may be formed in a cylindrical shape or various polygonal shapes. The shape of the first connection unit 121 may also be arbitrarily determined according to selection of a system designer.

The ultrasonic element unit 110 may be mounted to one surface 122a of the sound absorption material 122. In this case, one surface 122a of the sound absorption material 122 may also be formed in a planar shape. In addition, one surface 122a of the sound absorption material 122 may be formed as a curved surface having a predetermined curvature.

Referring to FIGS. 7 and 8, one or at least two seating units 125 in which the ultrasonic element unit 110 is seated may be mounted to one surface 122a of the sound absorption material 122. The seating unit 125 may include a seating surface 124 and a groove 123 formed in the vicinity of the seating surface 124. The ultrasonic element unit 110 may be disposed on the seating surface 124. In accordance with the embodiment, the ultrasonic transducer 113 may be disposed on the seating surface 124, or the acoustic enhancer 124 may be disposed thereon. The groove 123 may separate the seating surface 124 and other parts of one surface 122a from each other.

One end of the first connection unit 121 may be exposed on the seating surface 124. As described above, the first connection unit 121 may be formed to pass through the range from one surface 122a to the other surface of the sound absorption material 120. In this case, one first connection unit 121 may be exposed on the single seating surface 124. The first connection unit 121 may be exposed to the outside either at the center part of the seating surface 124 or in the vicinity of the center part of the seating surface 124. If the ultrasonic element unit 110 is seated on the seating surface 124, the first connection unit 121 may contact one end of the ultrasonic element unit 110. Therefore, the first connection unit 121 may be electrically coupled to the ultrasonic element unit 110.

The second electronic circuit 140 may be mounted to the other surface of the sound absorption material 122.

Figure 10:
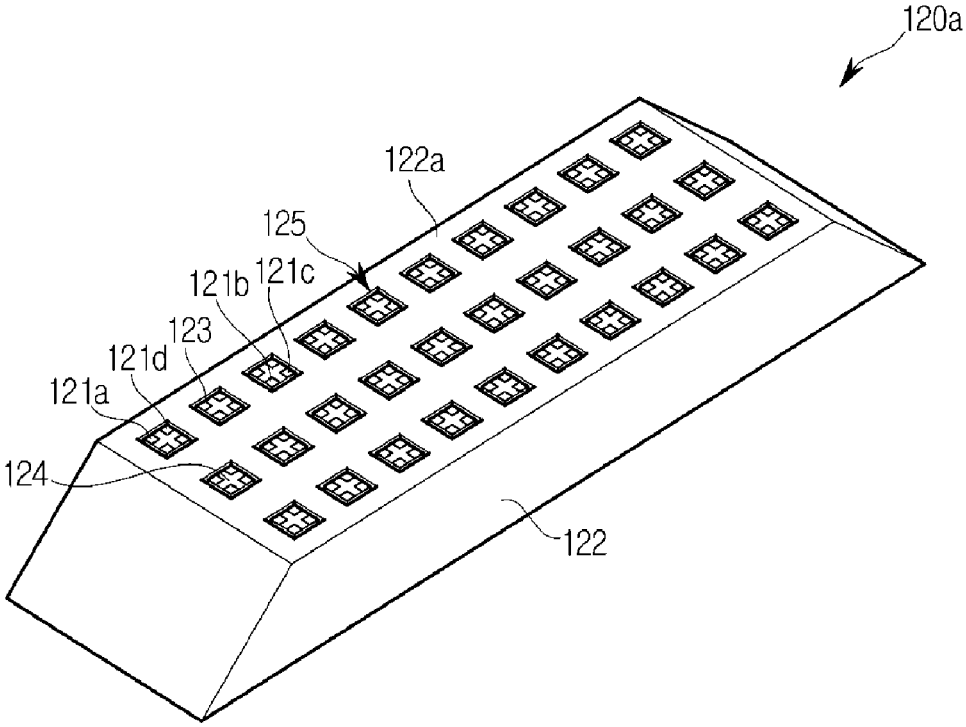
FIG. 10 is a perspective view illustrating a sound absorption unit according to a second embodiment of the present invention.
Figure 11:
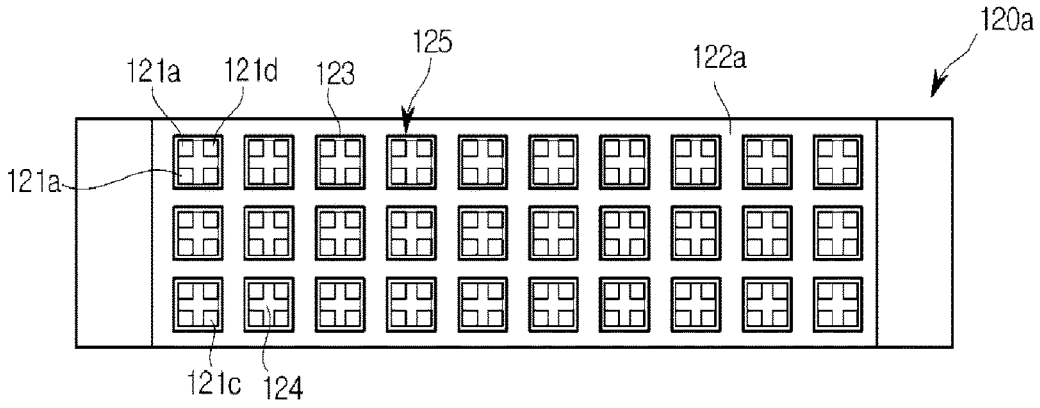
FIG. 11 is a plan view illustrating a sound absorption unit according to a second embodiment of the present invention.
Figure 12:
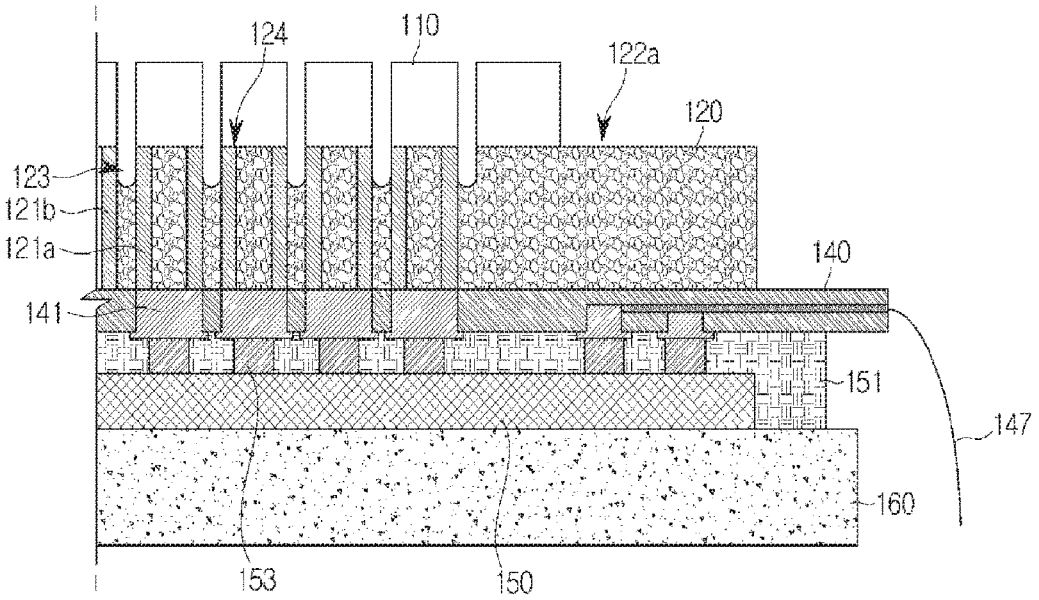
FIG. 12 is a lateral cross-sectional view illustrating a sound absorption unit according to a second embodiment of the present invention.
Figure 13:
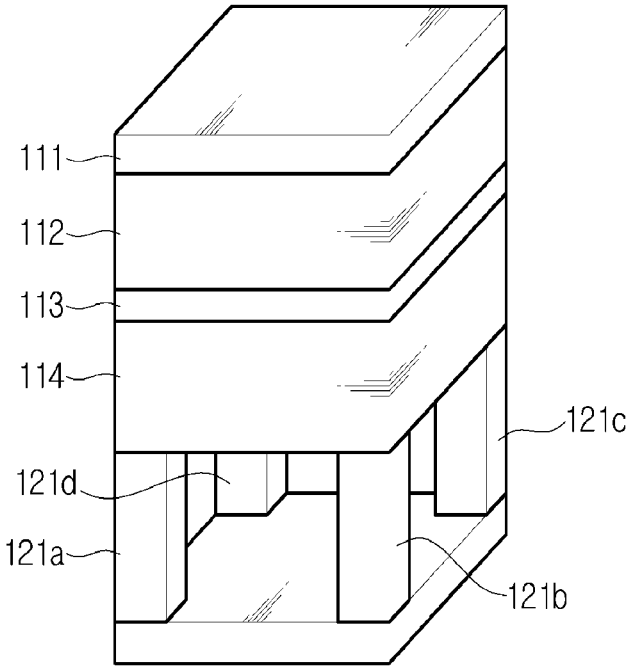
FIG. 13 is a view illustrating a sound absorption unit according to a second embodiment of the present invention.

FIG. 10 is a perspective view illustrating the sound absorption unit according to a second embodiment of the present invention. FIG. 11 is a plan view illustrating the sound absorption unit according to a second embodiment of the present invention. FIG. 12 is a lateral cross-sectional view illustrating the sound absorption unit according to a second embodiment of the present invention. FIG. 13 is a view illustrating the sound absorption unit according to a second embodiment of the present invention.

Referring to FIGS. 10 to 12, the sound absorption unit 120a of the second embodiment may include a sound absorption material 122, one surface 122a of which contacts the ultrasonic element unit 110 in the same manner as in the sound absorption unit 120 of the first embodiment. The first connection unit 121 may be configured to pass through the range from one surface 122a to the other surface of the sound absorption material 122.

One or at least two seating units 125 may be provided at one surface 122a of the sound absorption unit 120a of the second embodiment. The seating unit 125 may include a seating surface 124 and a groove 124 formed in the vicinity of the seating surface 124.

A plurality of first connection units (121a to 121d) may be exposed on the seating surface 124. As can be seen from FIGS. 10 to 13, each of the first connection units (121a to 121d) may be exposed to the outside at the corners of the seating surface 124. As can be seen from FIG. 13, if the ultrasonic element unit 110 is seated on the seating surface 124, the first connection units (121a to 121d) may contact one end of the ultrasonic element unit 110, and may contact, for example, one surface of the acoustic enhancer 114. In other words, the first connection units (121a to 121d) may support one ultrasonic element unit 110. Therefore, the first connection units (121a to 121d) may be electrically connected to the ultrasonic element unit 110.

The first connection units (121a to 121d) may have various shapes according to embodiments. For example, each of the first connection units (121a to 121d) may be formed in a prismatic or cylindrical shape. Besides, the first connection units (121a to 121d) may be selected by the system designer. An exposed surface of each first connection unit (121a to 121d) of the sound absorption unit 120a of the second embodiment may be identical in width to or be smaller or larger in width than the first connection unit 121 of the sound absorption unit 120 of the first embodiment.

The second electronic circuit 140 will hereinafter be described as an example of the substrate connection unit.

In accordance with the embodiment, the substrate connection unit may include the second electronic circuit 140.

Figure 14:
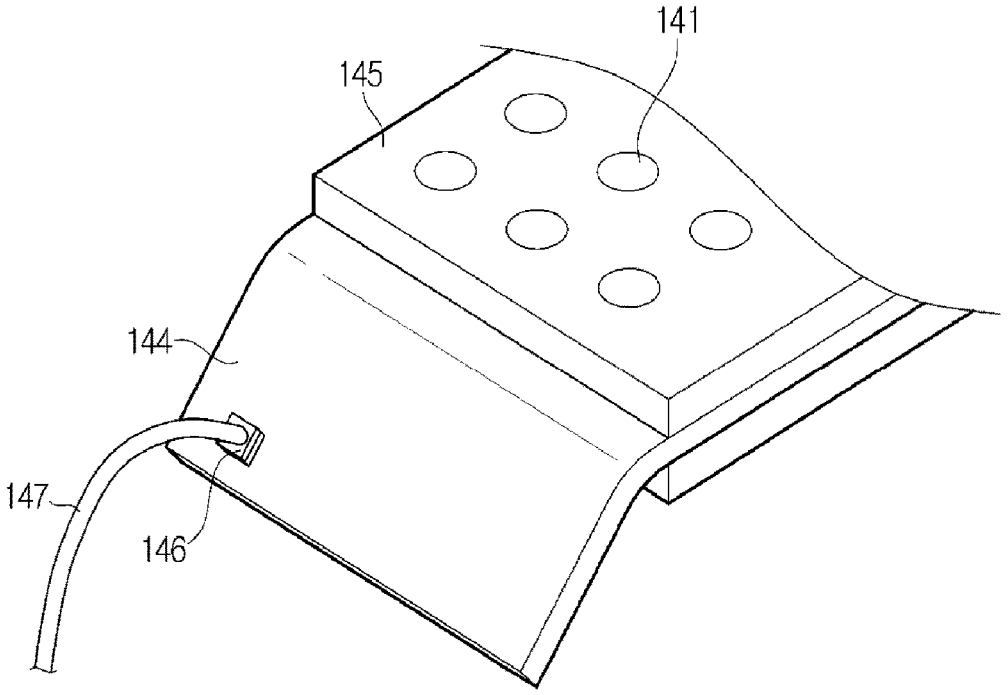
FIG. 14 is a view illustrating a second electronic circuit according to a first embodiment of the present invention.
Figure 15:
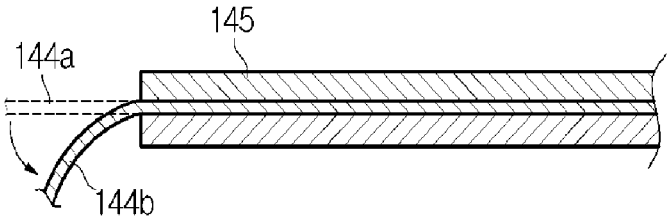
FIG. 15 illustrates a curved structure of a second electronic circuit.
Figure 16:
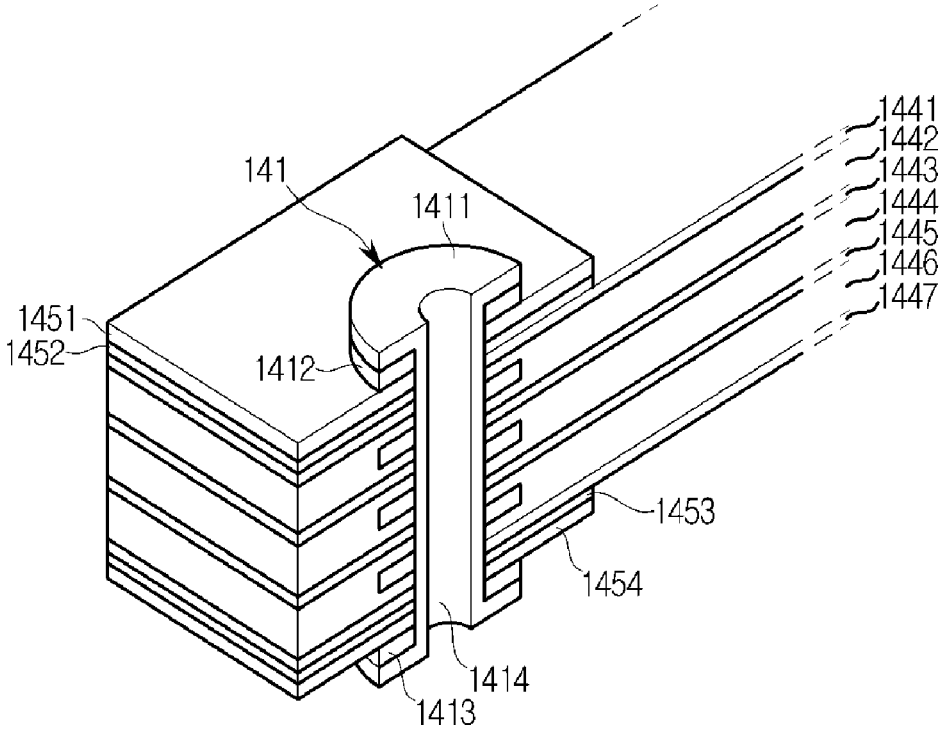
FIG. 16 is a cross-sectional view illustrating a second electronic circuit.

FIG. 14 is a view illustrating the second electronic circuit according to a first embodiment of the present invention. FIG. 15 illustrates a curved structure of the second electronic circuit. FIG. 16 is a cross-sectional view illustrating the second electronic circuit.

In accordance with the embodiment, the second electronic circuit 140 may include a substrate, various circuits formed on the substrate, and a semiconductor chip or other electronic components connected to the various circuits. In accordance with the embodiment, at least one of the substrate, the various circuits formed on the substrate, the semiconductor chip or other electronic components connected to the various circuits may be omitted as necessary.

Referring to FIG. 14, the substrate of the second electrical circuit 140 may be a rigid flexible PCB. The rigid flexible PCB may be a multi-layered substrate composed of a flexible PCB 144 and a rigid PCB 145. In more detail, the rigid flexible PCB may be implemented by overlapping the rigid substrate 145 with some parts of the flexible substrate 144.

The flexible substrate 144 may be easily bent, and the rigid substrate 145 may not be easily bent. Therefore, as shown in 144a and 144b of FIG. 15, one region (e.g., a first region) of the second electronic circuit 140 may be flexibly curved in various directions. The other region, for example, the second region, may not be curved. In this case, the statement that the above region is not curved does not indicate that the above region is not curved at all, but indicates that the above region is not generally used as a curved form.

An output unit 146 for communicating with the external part and its associated various circuits and electronic components may be mounted to the flexible substrate 144. A port coupled to the connector provided at the end of the external conductive line 147 may be included in the output unit 146.

For example, the flexible substrate 144 may have a multi-layered structure as shown in FIG. 16. In more detail, the flexible substrate 144 may include a plurality of polyimide cover layers (1441, 1447), a plurality of polyimide substrate layers (1443, 1445), and an adhesive layer to which the polyimide cover layers and the polyimide substrate layers are adhered.

Various electronic components related to control of the ultrasonic probe 100 may be mounted to the rigid substrate 145. The rigid substrate 145 may be formed of a rigid material 1451. The rigid material 1451 may be attached to the polyimide cover layers (1441, 1447) of the flexible substrate 144 through an adhesive. The substrate connection unit 141 may be formed on the rigid substrate 145.

As shown in FIGS. 4 and 16, the substrate connection unit 141 may pass through the second electronic circuit 140. In this case, the substrate connection unit 141 may pass through the flexible substrate 144 and the rigid substrate 145. The substrate connection unit 141 may be electrically coupled to the first electronic circuit 150.

Referring to FIG. 4, the substrate connection unit 141 may include a first substrate connection unit 142 configured to electrically interconnect the first connection unit 121 and the first electronic circuit 150; and a second substrate connection unit 143 configured to electrically interconnect the output unit 146 of the second electronic circuit 140 and the first electronic circuit 150.

One end of the first substrate connection unit 142 may contact a third connection unit 153 of the first electronic circuit 150, and the other end thereof may contact the first connection unit 121 of the sound absorption unit 120. Therefore, the first substrate connection unit 142 may be electrically coupled to the third connection unit 153 and the first connection unit 121. Therefore, the first substrate connection unit 142 may transmit the electrical signal generated from the third connection unit 153 of the first electronic circuit 150 to the first connection unit 121 of the sound absorption unit 120. The first substrate connection unit 142 may be provided at a specific part to which the flexible substrate 144 and the rigid substrate 145 are attached. In this case, the first substrate connection unit 142 may pass through both substrates (144, 145). The first substrate connection unit 142 may be concentrated at a specific position (see 'A' of FIG. 4) in such a manner that the first substrate connection unit 142 can contact the first connection unit 121 of the sound absorption unit 120.

One end of the second substrate connection unit 143 may be coupled to a fourth connection unit 154 of the first electronic circuit 150, and the other end or the center part of the second substrate connection unit 143 may be electrically coupled to the output unit 146. In this case, the second substrate connection unit 143 may be electrically connected to the output unit 146 through the second electronic circuit 140 (e.g., a circuit provided at a flexible substrate 144). The electrical signal generated from the fourth connection unit 154 of the first electronic circuit 150 may be applied to the output unit 146 through the second substrate connection unit 143. The second substrate connection unit 143 may pass through both substrates (144, 145) at a specific part to which the flexible substrate 144 and the rigid substrate 145 are attached. The second substrate connection unit 143 may be provided at a specific position (see 'B' of FIG. 4) at which the second substrate connection unit 143 does not contact the first connection unit 121 of the sound absorption unit 120. For example, the second substrate connection unit 143 may be installed at a specific position of the rigid substrate 145, where the specific position corresponds to the outer wall of the sound absorption unit 120.

Although only the mutual connection parts of the first substrate connection unit 142 and the second substrate connection unit 143 are different from each other, the first substrate connection unit 142 and the second substrate connection unit 143 may be identical in shape. Of course, according to some embodiments, the first substrate connection unit 142 may be different in shape from the second substrate connection unit 143 may be different from each other.

Various embodiments of the substrate connection unit 141 will hereinafter be described in detail.

Figure 17A:
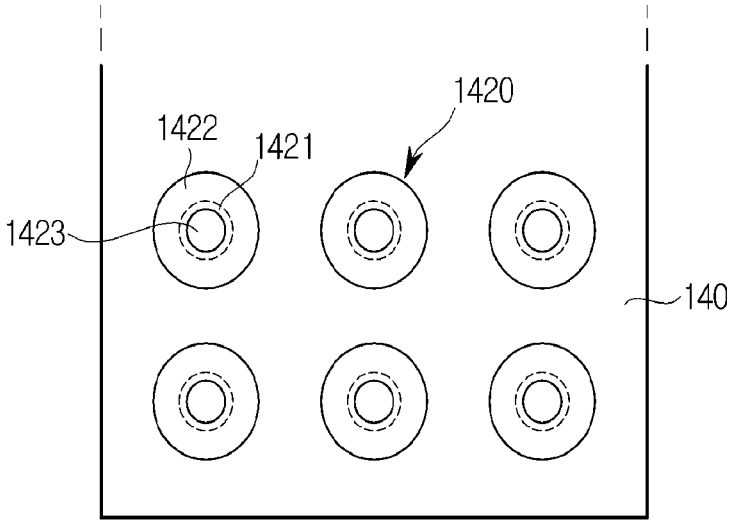
FIG. 17A is a plan view illustrating a second electronic circuit including a substrate connection unit according to a first embodiment of the present invention.
Figure 17B:
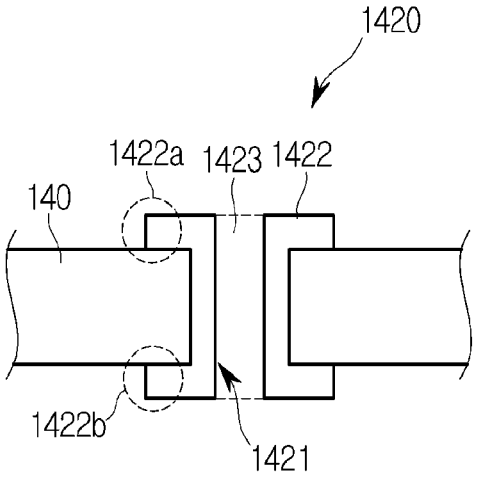
FIG. 17B is an exploded side view illustrating a second electronic circuit including a substrate connection unit according to a first embodiment of the present invention.

FIG. 17A is a plan view illustrating the second electronic circuit including the substrate connection unit according to a first embodiment of the present invention. FIG. 17B is an exploded side view illustrating the second electronic circuit including the substrate connection unit according to a first embodiment of the present invention.

The substrate connection unit 141 may include a via hole. As shown in FIGS. 17A and 17B, the substrate connection unit 1420 of the first embodiment may include a via hole. The via hole may include a first opening (also called a first aperture) 1421 that passes through the range from one surface to the other surface of the second electronic circuit 140, and a conductive material 1422 mounted to the inner lateral surface of the first opening 1421.

The first opening 1421 may have a circular shape from the viewpoint of a vertical upward direction of the second electronic circuit 140. In accordance with the embodiment, the first opening 1421 may have a polygonal shape such as a triangular or rectangular shape. In addition, the first opening 1421 may also have an elliptical shape. The first opening 1421 may be formed in the second electronic circuit 140 by puncturing the second electronic circuit 140 using a puncturing machine such as an electric drill.

The conductor 1422 may be provided at an inner lateral surface of the first opening 1421. In more detail, a conductive material such as metal is deposited on the inner lateral surface of the first opening 1421, so that the conductor 1422 may be provided at the inner lateral surface of the first opening 1421. A second opening 1423 may further be formed at the center part of the conductor 1422. The second opening 1423 may have a circular or polygonal shape. In addition, the conductor 1422 may protrude in the opposite direction from the center part of the second opening 1423 at both surfaces of the second electronic circuit 140, and some parts of both surfaces of the second electronic circuit 140 may be deposited as shown in 1422a and 1422b.

Figure 18A:
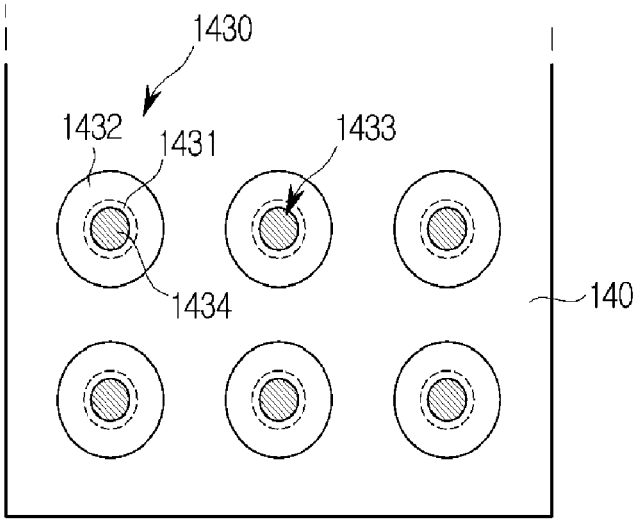
FIG. 18A is a plan view illustrating a second electronic circuit including a substrate connection unit according to a second embodiment of the present invention.
Figure 18B:
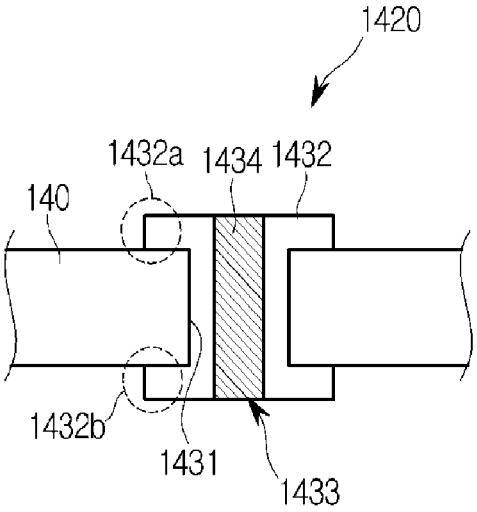
FIG. 18B is an exploded side view illustrating a second electronic circuit including a substrate connection unit according to a second embodiment of the present invention.

FIG. 18A is a plan view illustrating the second electronic circuit including the substrate connection unit according to a second embodiment of the present invention. FIG. 18B is an exploded side view illustrating the second electronic circuit including the substrate connection unit according to a second embodiment of the present invention.

Referring to FIGS. 18A and 18B, the substrate connection unit 1430 of the second embodiment may include a first opening 1431 configured to pass through the range from one surface to the other surface of the second electronic circuit 140; a conductor 1432 formed at the inner lateral surface of the first opening 1431 and including a second opening 1433 formed at an inner surface; and a filter 1434 configured to shield the second opening 1433.

In the same manner as described above, the first opening 1431 may have a polygonal shape such as a circular, triangular, or rectangular shape or other shapes such as an elliptical shape from the viewpoint of a vertical upward direction of the second electronic circuit 140. The first opening 1431 may be formed in the second electronic circuit 140 by puncturing the second electronic circuit 140.

The conductor 1432 may be provided at the inner lateral surface of the first opening 1431 by depositing a conductive material on the inner lateral surface of the first opening 1431. The second opening 1433 provided at the conductor 1432 may have a circular or polygonal shape.

The filling material 1434 is inserted into the second opening 1433 so as to shield the second opening 1433. The filling material 1434 may be formed of a material having no conductivity. The filling material 1434 may also be formed of any of various synthetic resins.

In the case of the substrate connection unit 1430 of the second embodiment, the conductor 1432 protrudes in the opposite direction from the center part of the second opening 1433 at both surfaces of the second electronic circuit 140, and some parts of both surfaces of the second electronic circuit 140 may be deposited as shown in 1432a and 1432b.

Figure 19A:
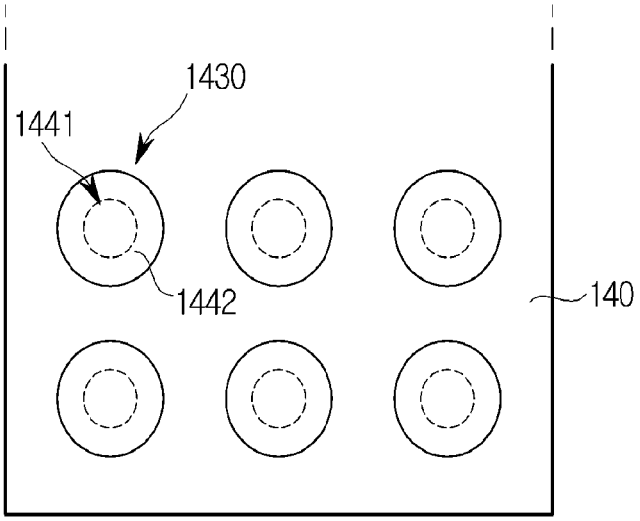
FIG. 19A is a plan view illustrating a second electronic circuit including a substrate connection unit according to a third embodiment of the present invention.
Figure 19B:
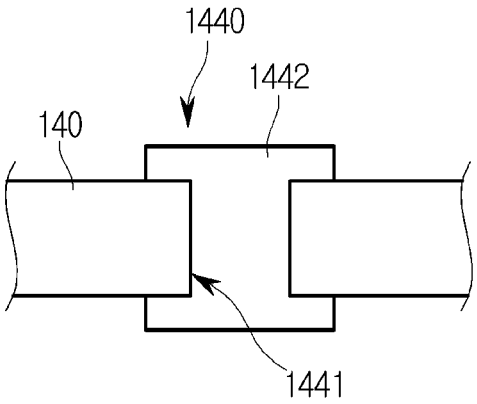
FIG. 19B is an exploded side view illustrating a second electronic circuit including a substrate connection unit according to a third embodiment of the present invention.

FIG. 19A is a plan view illustrating the second electronic circuit including the substrate connection unit according to a third embodiment of the present invention. FIG. 19B is an exploded side view illustrating the second electronic circuit including the substrate connection unit according to a third embodiment of the present invention.

Referring to FIGS. 19A and 19B, the substrate connection unit 1440 of the third embodiment may include a first opening 1441 configured to pass through the range from one surface to the other surface of the second electronic circuit 140; and a conductor 1442 provided at the inner surface of the first opening 1441. The conductor 1442 may completely shield the first opening 1441. In other words, the conductor 1442 may not form the second openings (1423, 1433) as described above.

In the same manner as described above. the first opening 1441 may have various shapes, and may be formed in the second electronic circuit 140 using a puncturing machine.

Figure 20A:
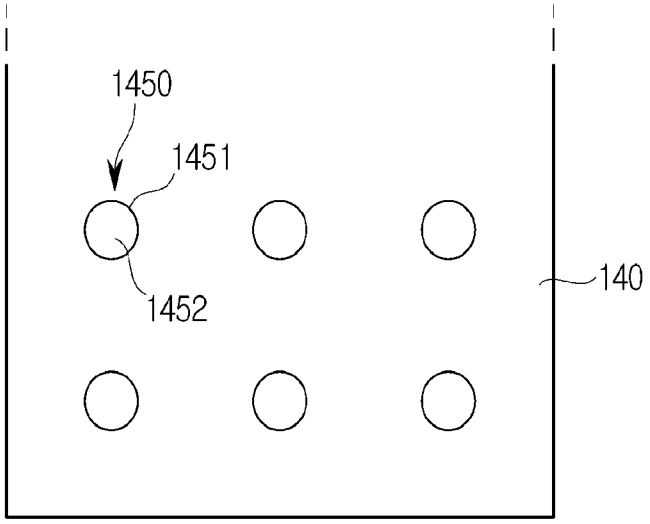
FIG. 20A is a plan view illustrating a second electronic circuit including a substrate connection unit according to a fourth embodiment of the present invention.
Figure 20B:
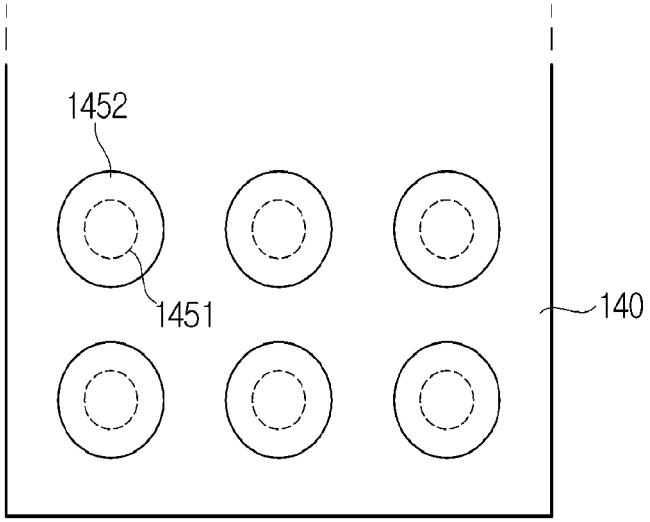
FIG. 20B is a bottom view illustrating a second electronic circuit including a substrate connection unit according to a fourth embodiment of the present invention.
Figure 20C:
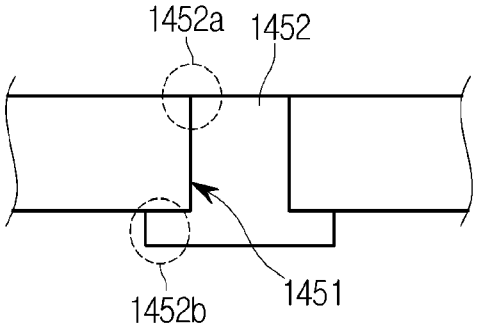
FIG. 20C is an exploded side view illustrating a second electronic circuit including a substrate connection unit according to a fourth embodiment of the present invention.

FIG. 20A is a plan view illustrating the second electronic circuit including the substrate connection unit according to a fourth embodiment of the present invention. FIG. 20B is a bottom view illustrating the second electronic circuit including the substrate connection unit according to a fourth embodiment of the present invention. FIG. 20C is an exploded side view illustrating the second electronic circuit including the substrate connection unit according to a fourth embodiment of the present invention.

Referring to FIGS. 20A to 20C, the substrate connection unit 1450 of the fourth embodiment may include a first opening 1451 configured to pass through the range from one surface to the other surface of the second electronic circuit 140; and a conductor 1452 installed at the inner lateral surface of the first opening unit 1451.

In the same manner as described above, the first opening 1451 may have various shapes, and may be formed in the second electronic circuit 140 using the puncturing machine.

The conductor 1452 may be provided at the inner lateral surface of the first opening 1451 by depositing a metal material or the like on the inner lateral surface of the first opening 1451. The second openings (1423, 1433) may be formed at a center part of the conductor 1452, or may not be formed at the center part of the conductor 1452.

Meanwhile, the conductor 1452 may protrude in the opposite direction form the center part of the second opening 1423 at only one surface of the second electronic circuit 140 (see 1452b). In other words, the conductor 1452 may not be deposited on any one surface of the second electronic circuit 140, or may be deposited only on the other surface of the second electronic circuit 140.

Figure 21:
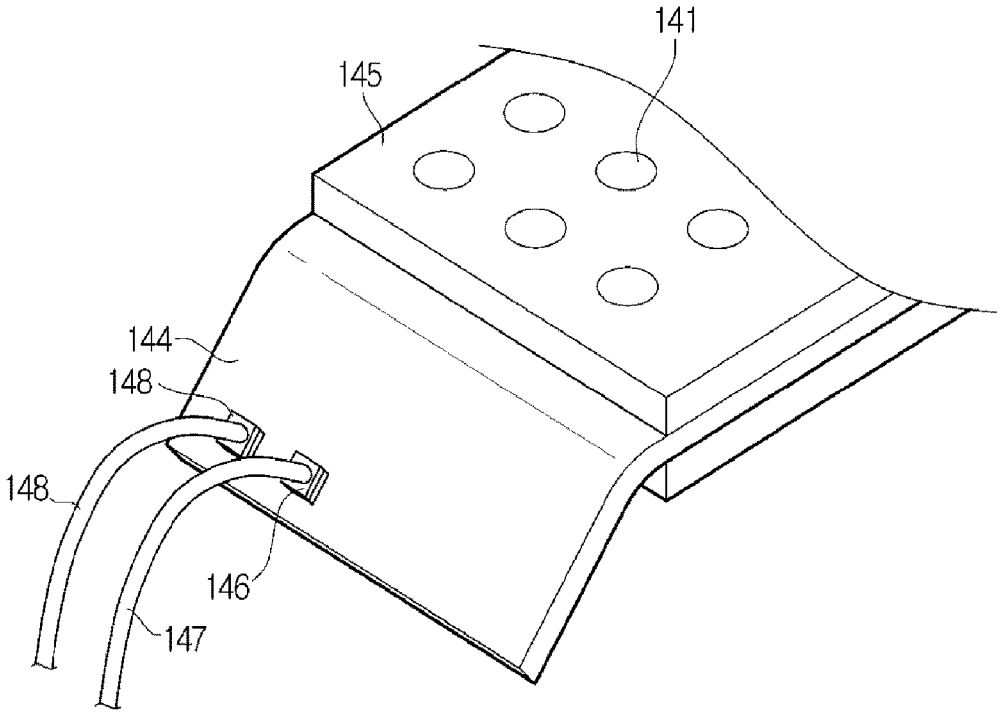
FIG. 21 is a view illustrating a second electronic circuit according to a second embodiment of the present invention.

FIG. 21 is a view illustrating a second electronic circuit according to a second embodiment of the present invention.

Referring to FIG. 21, the second electronic circuit 140 may include a plurality of output units (146, 148). The output units (146, 148) may be provided at the flexible substrate 145. The output units (146, 148) may output different electrical signals, and may transmit the different electrical signals to the main body 200. The respective output units (146, 148) may be connected to different second substrate connection units 143. The different second substrate connection units 143 may transmit the electrical signals generated from the first electronic circuit 150 to the respective output units (146, 148).

The first electronic circuit will hereinafter be described in detail.

Figure 22A:
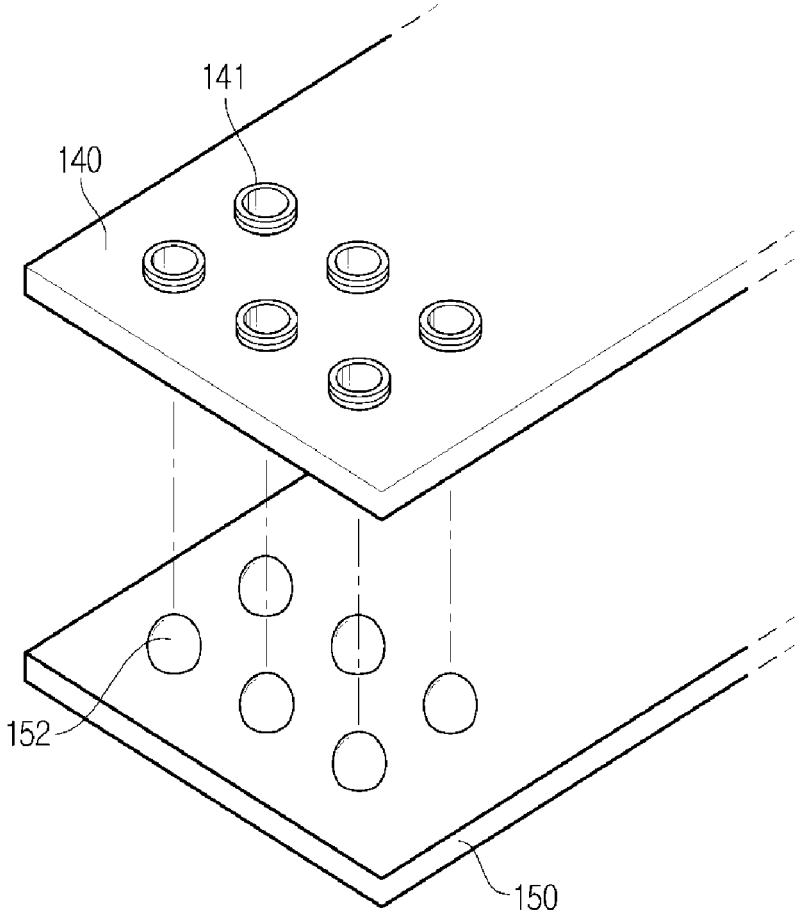
FIG. 22A is a perspective view illustrating a first electronic circuit according to an embodiment of the present invention.
Figure 22B:
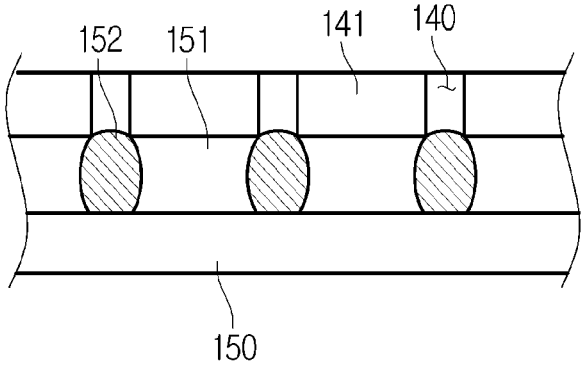
FIG. 22B is a view illustrating a first electronic circuit according to an embodiment of the present invention.

FIG. 22A is a perspective view illustrating a first electronic circuit according to an embodiment of the present invention. FIG. 22B is a view illustrating the first electronic circuit according to an embodiment of the present invention.

In accordance with the embodiment, the first electronic circuit 150 may include a substrate, various circuits formed on the substrate, and a semiconductor chip and various electronic components connected to the various circuits. For example, the first electronic circuit 150 may include at least one Application Specific Integrated Circuit (ASIC). In accordance with the embodiment, at least one of the substrate of the first electronic circuit 150, various circuits formed on the substrate, and a semiconductor chip and various electronic components connected to the various circuits may be omitted for convenience of description.

Referring to FIGS. 4, 22A and 22B, one surface of the first electronic circuit 150 may contact one surface of the second electronic circuit 140. In more detail, the first electronic circuit 150 may be mounted to a surface at which a support 120 of the second electronic circuit 140 is not installed.

One or at least two second connection units 152 may be provided at the first electronic circuit 150. The second connection unit 152 may be formed of a conductive metal material such as gold (Au) or lead (Pb). The second connection unit 152 may be implemented as a bump. The second connection unit 152 implemented as a bump may be, for example, a solder ball. A thin electrode may also be provided at one end of the second connection unit 152.

The second connection unit 152 may electrically contact the substrate connection unit 141 of the second electronic circuit 140. In this case, the thin electrode may also contact the substrate connection unit 141. Since the second connection unit 152 contacts the substrate connection unit 141 of the second electronic circuit 140, the first electronic circuit 150 and the second electronic circuit 140 may be electrically interconnected by the substrate connection unit 141 and the second connection unit 152. The second connection unit 152 contained in the first electronic circuit 150 may have a position corresponding to the substrate connection unit 141 of the second electronic circuit 140, and the number of second connection units 152 contained in the first electronic circuit 150 may correspond to the number of the substrate connection units 141 of the second electronic circuit 140.

Referring to FIG. 22B, the first electronic circuit 150 and the second electronic circuit 140 may be adjacent to each other on the basis of a predetermined gap. A separation unit 151 may be disposed between the first electronic circuit 150 and the second electronic circuit 140. The separation unit 151 may prevent the first electronic circuit 150 from directly contacting the second electronic circuit 140. The separation unit 151 may be formed of a nonconductive material. For example, the separation unit 151 may also be formed of epoxy resin. The epoxy resin may provide an adhesive function, and the second electronic circuit 140 and the first electronic circuit 150 may be adhered to each other using the separation unit 151 formed of epoxy resin.

Referring to FIG. 22B, the second connection unit 152 may pass through the separation unit 151 so that it may protrude toward the outside of the separation unit 151. In other words, the first electronic circuit 150 and various electronic components mounted to the first electronic circuit 150 may be shielded by the separation unit 151 formed of epoxy resin, so that they are not exposed to the outside. However, only the second connection unit 152 may be exposed to the outside of the separation unit 151. The second connection unit 152 protruding toward the outside may contact the substrate connection unit 141.

The separation unit 151 may be disposed between the first electronic circuit 150 and the second electronic circuit 140 using various methods.

For example, the first electronic circuit 150 and the second electronic circuit are located close to each other in such a manner that the second connection unit 152 contacts the substrate connection unit 141, and a gap formed between the first electronic circuit 150 and the second electronic circuit is filled with epoxy resin, so that the separation unit 151 may be disposed between the first electronic circuit 150 and the second electronic circuit.

In another example, after the epoxy resin is deposited on the first electronic circuit 150 having the second connection unit 152 in such a manner that some parts of the second connection unit 152 are exposed to the outside, the second electronic circuit 140 is installed on the epoxy resin, so that the separation unit 151 may be disposed between the first electronic circuit 150 and the second electronic circuit.

The second connection unit 152 may include a third connection unit 153 contacting a first substrate connection unit 142 and a fourth connection unit 154 contacting a second substrate connection unit 143. The second connection unit 153 may be provided at a specific position at which the second connection unit 153 can contact the first substrate connection unit 142. The second connection unit 154 may be provided at a specific position at which the second connection unit 154 can contact the second substrate connection unit 143.

The first electronic circuit 150 may include a semiconductor chip acting as the first processor 130 and electronic components associated with the semiconductor chip. The first processor 130 may be installed at a substrate of the first electronic circuit 150. The second connection unit 152 may be provided at the first electronic circuit 150, and may be disposed on the circuit electrically connected to the first processor 130, so that the second connection unit 152 may be electrically connected to the first processor 130. The electrical signals generated from not only the semiconductor chip acting as the first processor 130 but also the associated components may be applied to the substrate connection unit 141 or the output unit 146 through the second connection unit 152. For example, the electrical signals (e.g., ultrasonic signals) transferred through the substrate connection unit 141 may be applied to the first processor 130 through the second connection unit 152.

Figure 22C:
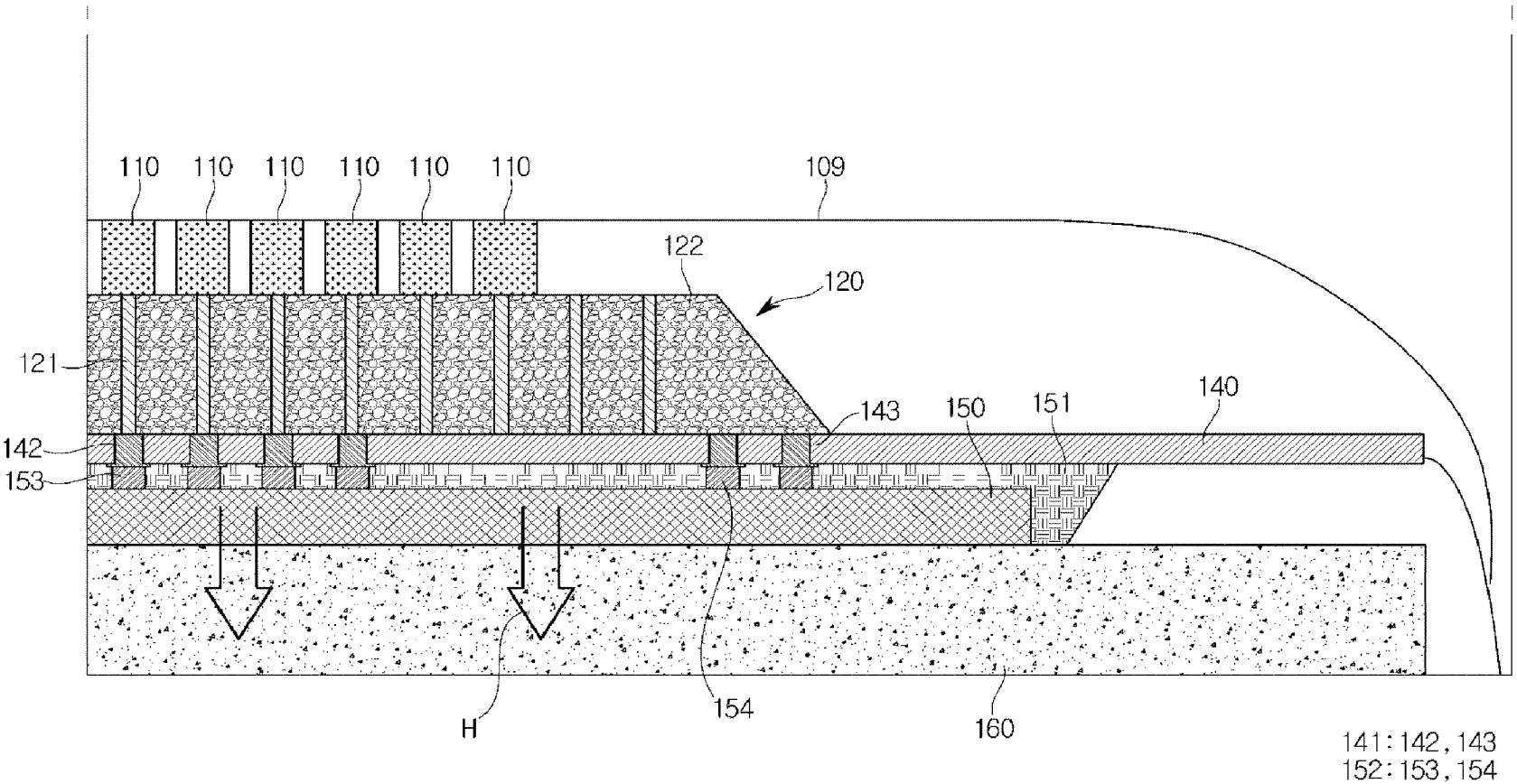
FIG. 22C is a view illustrating a heat conduction unit installed at a back surface of the first electronic circuit.

FIG. 22C is a view illustrating a heat conduction unit installed at a back surface of the first electronic circuit.

Referring to FIG. 4, the second electronic circuit 140 may be attached to one surface of the first electronic circuit 150, and the heat conduction unit 160 may be installed at the other surface of the first electronic circuit 150. The heat conduction unit 160 may be attached to the other surface of the first electronic circuit 150 using an adhesive or the like. Referring to FIG. 22C, if the first processor 130 or the like installed at the first electronic circuit 150 performs data calculation processing, heat may occur in the first electronic circuit 150. The generated heat may cause malfunction of the first electronic circuit 150 or may cause malfunction of other electronic components (e.g., the second electronic circuit 140) disposed in the vicinity of the first electronic circuit 150.

The heat conduction unit 160 may emit the heat generated from the first electronic circuit 150 to the outside. In more detail, after heat generated from the first electronic circuit 150 is transferred to the heat conduction unit 160, the heat may emit in the air along the heat conduction unit 160.

The heat conduction unit 160 may be implemented using various heat conductive materials. For example, the heat conduction unit 160 may be formed of graphite, tungsten, tungsten oxide, silicon, aluminum oxide, glass microballoon filling material, or the like.

A process of radiating ultrasonic waves using the above-mentioned ultrasonic probe 100, a process for receiving ultrasonic waves and converting the received ultrasonic waves into an electrical signal, and a process for transferring the electrical signal to the main body 200 will hereinafter be described in detail.

Figure 23A:
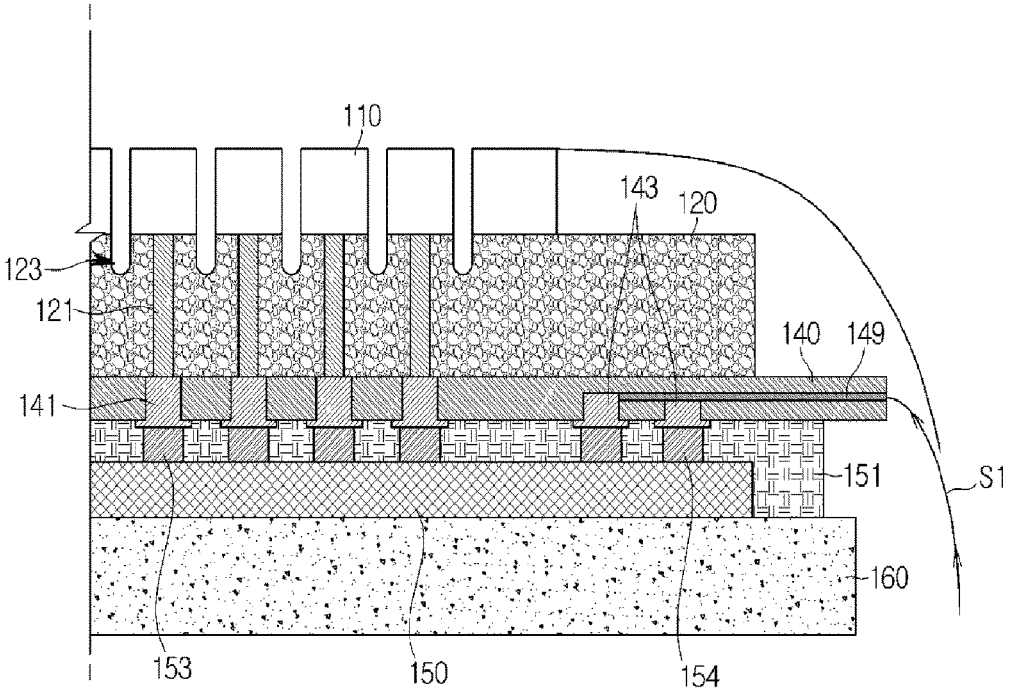
FIG. 23A is a conceptual diagram illustrating a process for transmitting a control signal to a first processor mounted to an ultrasonic probe.
Figure 23B:
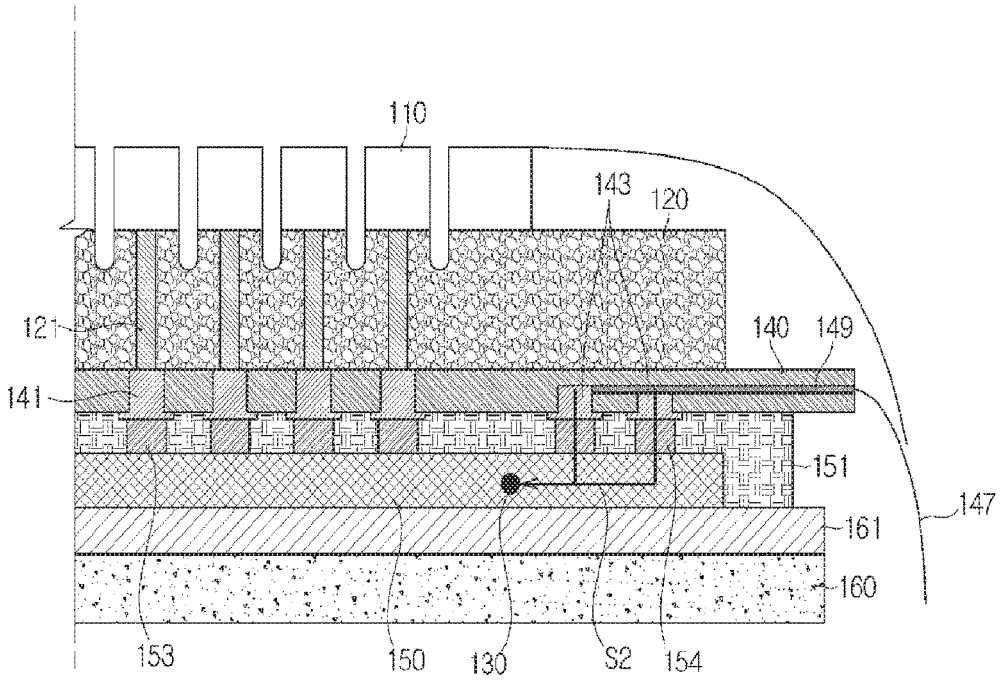
FIG. 23B is a conceptual diagram illustrating a process for transmitting a control signal to a first processor mounted to an ultrasonic probe.
Figure 23C:
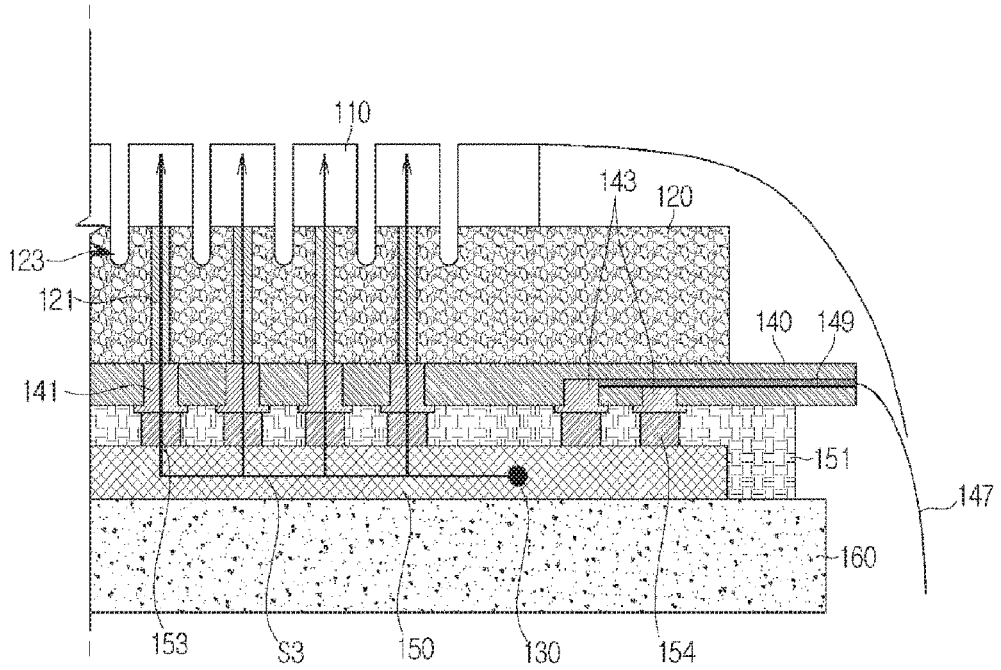
FIG. 23C is a conceptual diagram illustrating a process for transmitting a control signal to an ultrasonic element.
Figure 24:
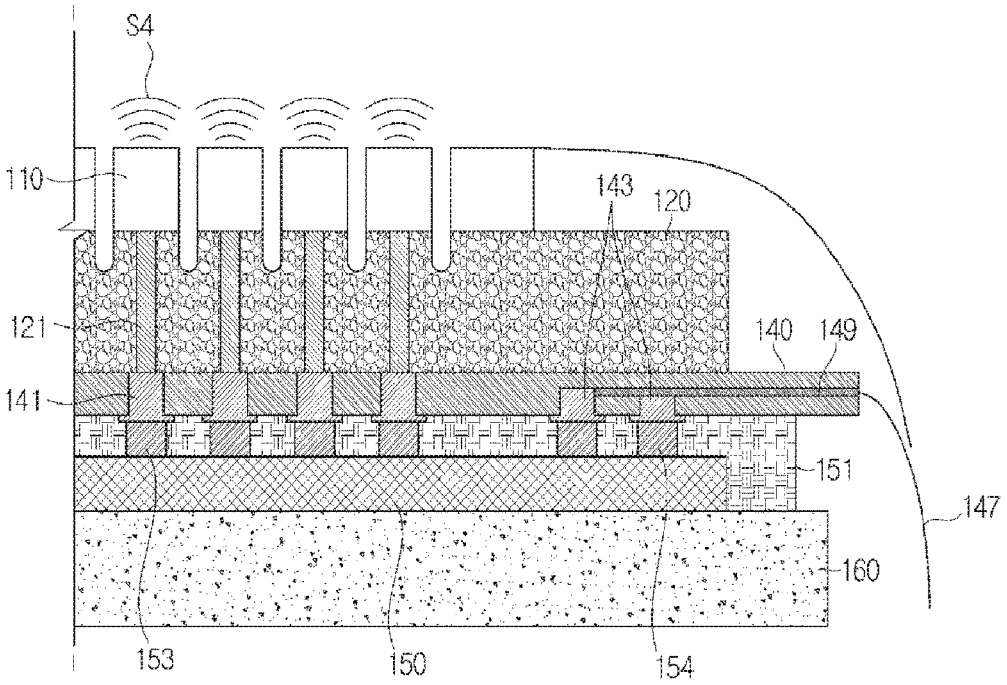
FIG. 24 is a conceptual diagram illustrating a process for irradiating ultrasonic waves using an ultrasonic element.

FIG. 23A is a conceptual diagram illustrating a process for transmitting a control signal to the first processor mounted to the ultrasonic probe. FIG. 23B is a conceptual diagram illustrating the process for transmitting a control signal to the first processor mounted to the ultrasonic probe. FIG. 23C is a conceptual diagram illustrating a process for transmitting a control signal to the ultrasonic element. FIG. 24 is a conceptual diagram illustrating a process of radiating ultrasonic waves using the ultrasonic element.

Referring to FIG. 23A, if the controller 220 of the main body 200 outputs a control signal, the control signal may be applied to the circuit 149 contained in the second electronic circuit 140 through the cable 93 and the conductive line 147 (S1). Referring to FIG. 23B, the control signal received through the conductive line 147 may be applied to the first processor 130 contained in the first electronic circuit 150 through not only the second substrate connection unit 143 connected to the circuit 149 but also the fourth connection unit electrically connected to the second substrate connection unit 143 (S2).

Referring to FIG. 23C, the first processor 130 contained in the first electronic circuit 150 may output a control command related to ultrasonic irradiation as an electrical signal format. The electrical signal may be a pulse having a predetermined frequency. The output control command may be applied to one or at least two third connection units 153 through the circuit of the first electronic circuit 150.

Referring to FIG. 23C, the electrical signals received by the third connection unit 153 may pass through the second electronic circuit 140 through the substrate connection unit 141 attached to the third connection unit 153, for example, through the first substrate connection unit 142. After the electrical signal passes through the second electronic circuit 140, the electrical signal may be applied to the first connection unit 121 provided at the sound absorption unit 120. The electrical signal applied to the first connection unit 121 may be transmitted to the ultrasonic element unit 110 along the first connection unit 121 (S3).

Referring to FIG. 24, if the electrical signal is applied to the ultrasonic element unit 110, the ultrasonic transducer 113 (e.g., a piezoelectric element) of the ultrasonic element unit 110 may be vibrated according to the received electrical signal so as to generate ultrasonic waves (S4). The generated ultrasonic waves are emitted to the outside. The generated ultrasonic waves may be emitted in the direction of the object 99. Meanwhile, the generated ultrasonic waves may also be emitted in the direction of the sound absorption unit 120. In this case, the sound absorption unit 120 may absorb ultrasonic waves emitted in the direction of the sound absorption unit 120.

Figure 25:
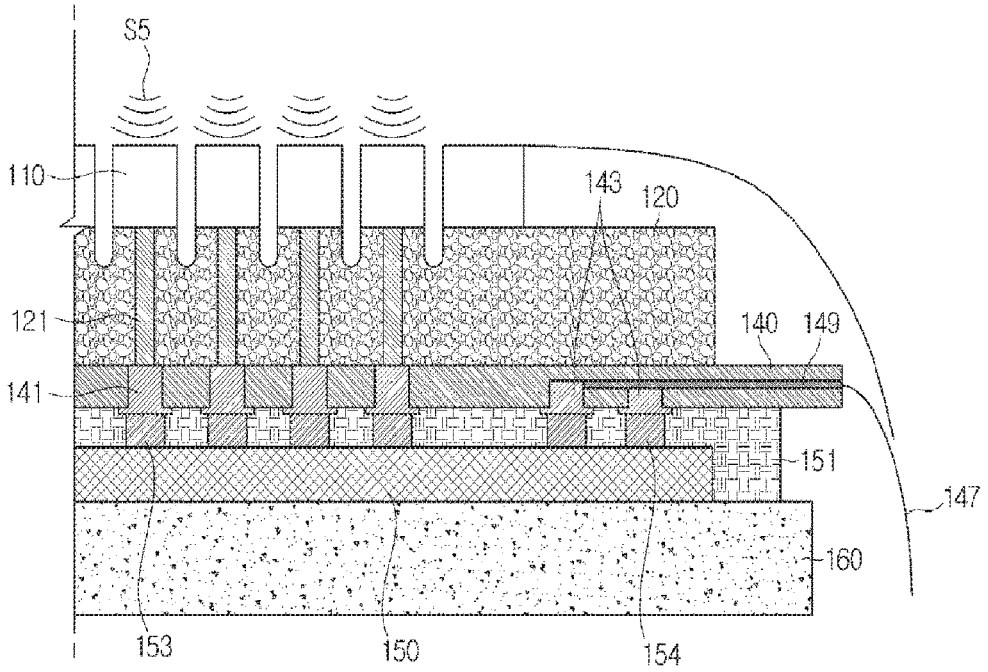
FIG. 25 is a conceptual diagram illustrating a process for receiving ultrasonic waves using an ultrasonic element.
Figure 26:
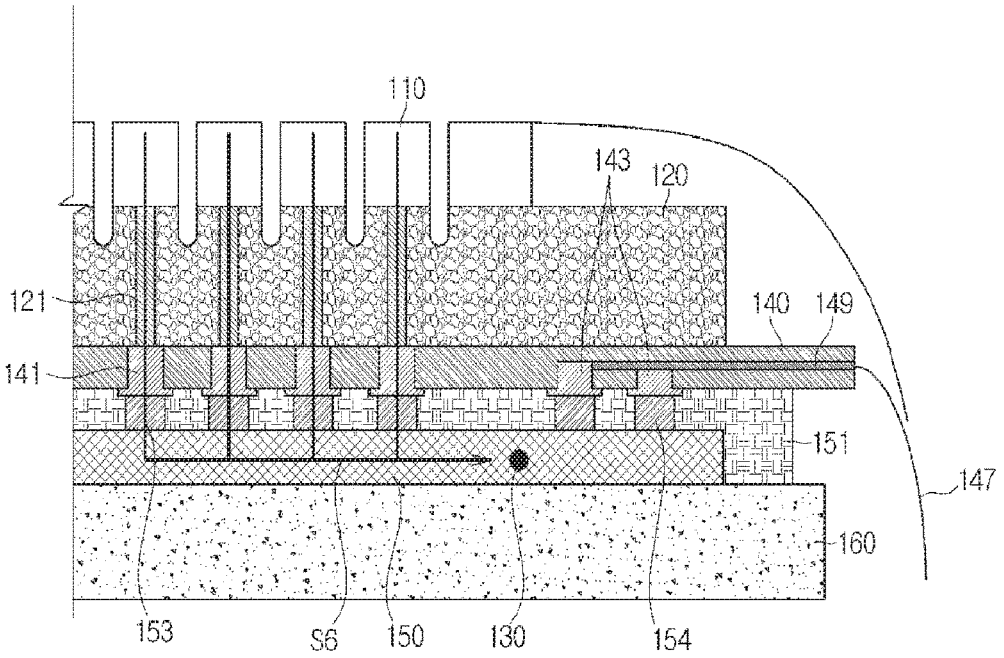
FIG. 26 is a conceptual diagram illustrating a transmission process of an electrical signal corresponding to ultrasonic waves received by the ultrasonic element

FIGS. 25 and 26 are conceptual diagrams illustrating a process for receiving ultrasonic waves using the ultrasonic element.

Referring to FIGS. 25 and 26, the ultrasonic element unit 110 may receive ultrasonic waves from the external part (S5). The ultrasonic waves received from the external part may be obtained when ultrasonic waves generated from the ultrasonic element unit 110 are reflected from the target site 98 contained in the object 99. In accordance with the embodiment, the ultrasonic waves received from the external part may be generated from the target site 98 by irradiating laser or the like to the target site 98.

The ultrasonic transducer 113 of the ultrasonic element unit 110 may be vibrated with a frequency corresponding to a frequency of the received ultrasonic waves. so as to output the alternating current (AC) electrical signal. The electrical signal may be transmitted to the processor 130 along an opposite path of the ultrasonic irradiation case (S6). In more detail, the electrical signal generated from the ultrasonic element unit 110 may be applied to the first processor 130 through the first connector 121 provided at the sound absorption unit 120, the first substrate connection unit 142, the third connection unit 153, and a circuit contained in the first electronic circuit 150.

The first processor 130 may amplify the received electrical signal, perform analog-to-digital conversion (ADC) of the amplified signal, and perform beamforming for focusing multi-channel electric signals generated from the respective ultrasonic element units 110. The beamformed signals may be temporarily stored in a storage unit (e.g., RAM) for assisting the first processor 130.

Figure 27:
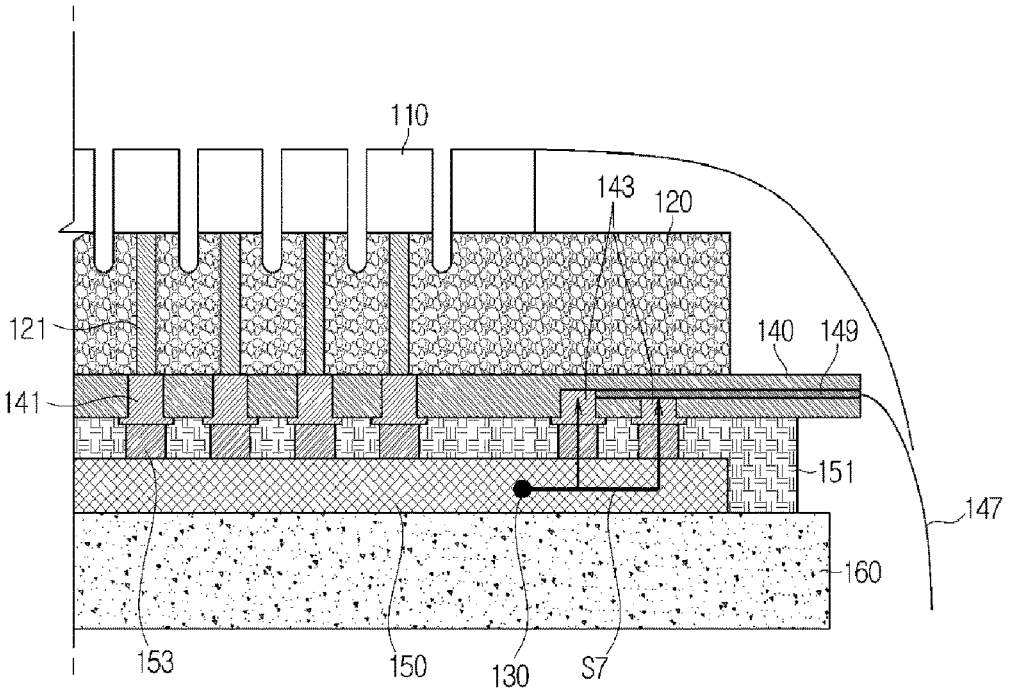
FIG. 27 is a conceptual diagram illustrating a process for transmitting processed signals to a main body.
Figure 28:
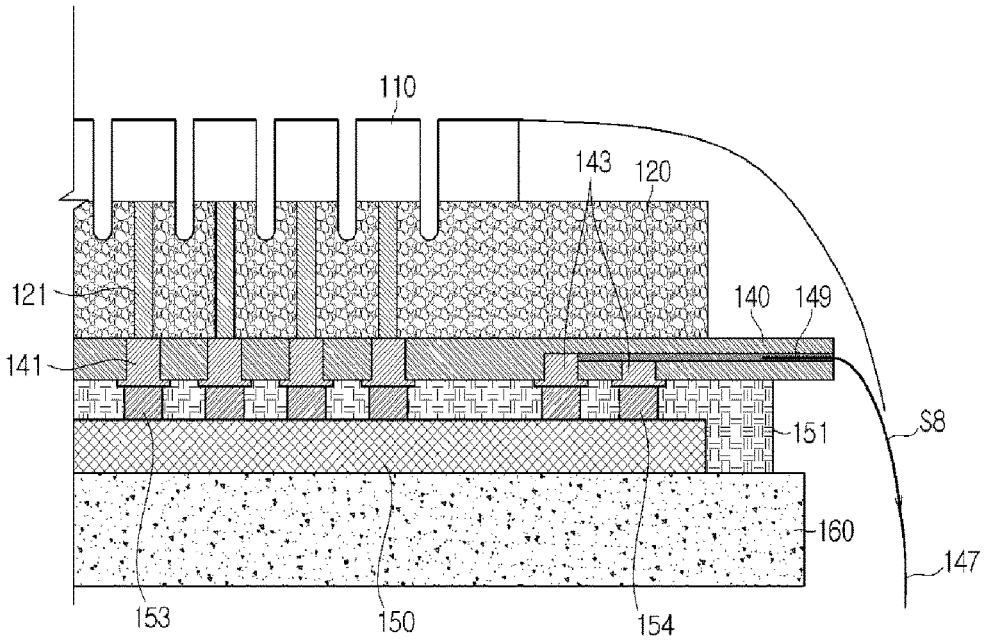
FIG. 28 is a conceptual diagram illustrating a process for transmitting processed signals to a main body.

FIGS. 27 and 28 are conceptual diagrams illustrating a process for transmitting processed signals to the main body.

The first processor 130 may output the beamformed signal, and the beamformed signal may be applied to the fourth connection unit 143 along the circuit provided in the first electronic circuit 150. The beamformed signal applied to the fourth connection unit 143 may be transmitted to the second substrate connection unit 143 contacting the fourth connection unit 143 (S7). The beamformed signal may be applied to the output unit 146 through the circuit 149 coupled to the second substrate connection unit 143.

The beamformed signal is output through the output unit 146, and may be applied to the main body 200 through the conductive line 147 and the cable 93 connected to the output unit 146 (S8). The main body 200 may perform signal processing and image processing of the received beamformed signal, may generate an ultrasound image corresponding to the beamformed signal, and may display the ultrasound image on the display unit 280 for user recognition.

A process for fabricating the sound absorption unit will hereinafter be described with reference to FIGS. 29 and 30.

Figure 29:
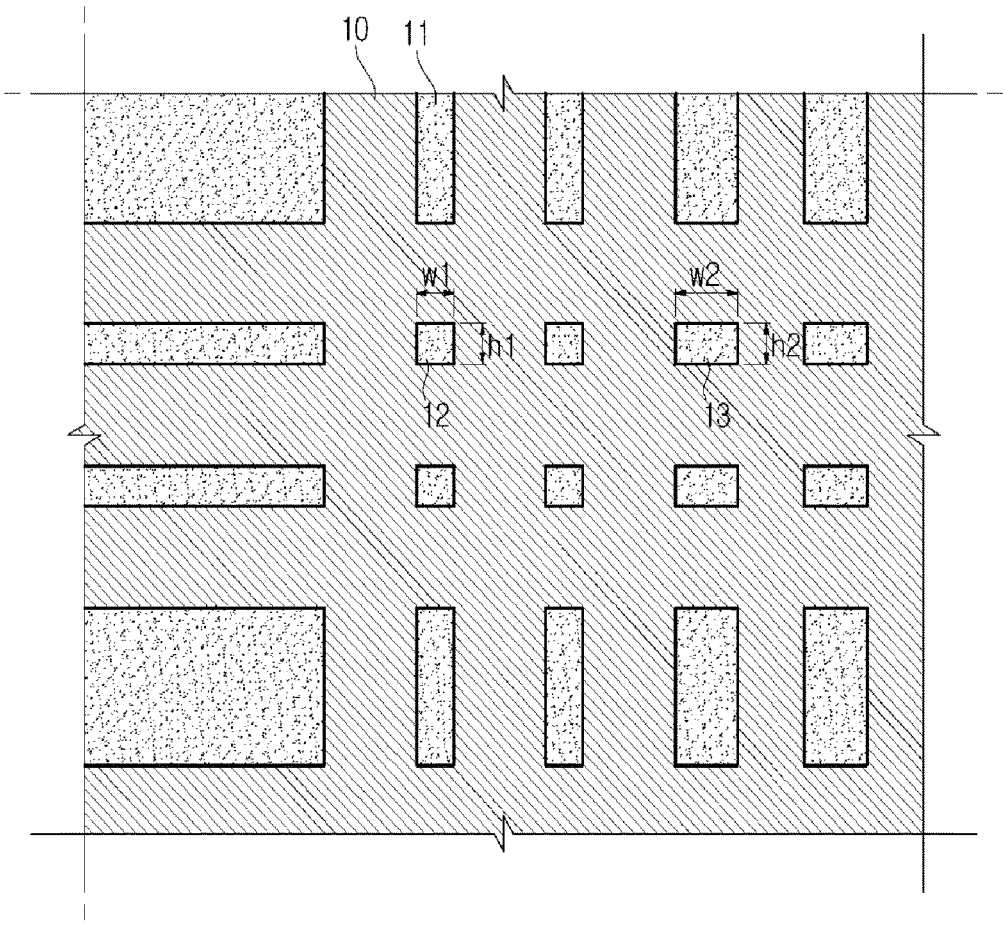
FIG. 29 is a conceptual diagram illustrating a process for fabricating a sound absorption unit.
Figure 30:
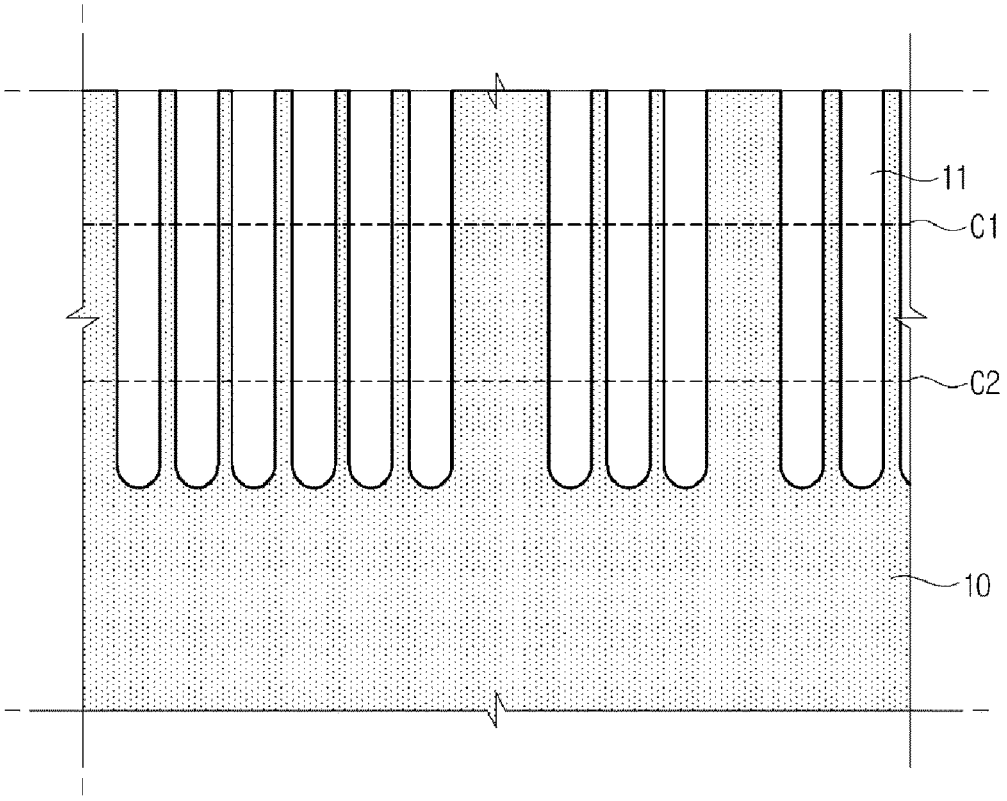
FIG. 30 is a conceptual diagram illustrating a process for fabricating a sound absorption unit.

FIGS. 29 and 30 are conceptual diagrams illustrating the process for fabricating the sound absorption unit. FIG. 29 is a plan view illustrating the sound absorption material 10 in which the conductor 11 is inserted. FIG. 30 is a lateral cross-sectional view illustrating the sound absorption material 10 in which the conductor 11 is inserted. For convenience of description and better understanding of the present invention, an upper part of FIG. 30 will hereinafter be referred to as an upward direction, and a direction from the upper part to the lower part of FIG. 30 will hereinafter be referred to as a vertical direction. In addition, a specific direction orthogonal to the vertical direction will hereinafter be referred to as a horizontal direction.

As can be seen from FIG. 29, the conductor 11 may be inserted into the sound absorption material 10, and the conductor 11 may be diced as necessary. The inserted conductor 11 may be used as the above-mentioned support connection unit 121.

From the viewpoint of the upward direction, the conductor 12 may be diced to have a square shape. The width (w1) or the height (h1) of the conductor 11 may be designed in various ways according to selection of the system designer. For example, the width (w1) of the conductor 11 may be 50 micrometers (μm), and the height (h1) of the conductor 11 may be 50 micrometers (μm). In addition, the conductor 13 may be diced to have a rectangular shape. In this case, the conductor 13 may have various widths (w2) and heights (h2) according to selection of the system designer. For example, the width (w2) of the conductor 12 may be 60 micrometers (μm), and the height (h2) of the conductor 12 may be 50 micrometers (μm).

If the conductor 11 is inserted into the sound absorption material 10, the sound absorption material 10 is severed in a horizontal direction so that both ends of the conductor 11 are exposed to the outside, as shown in FIG. 30. In more detail, the sound absorption material 10 is cut along the first sectional surface (c1) and the second sectional surface (c2) shown in FIG. 30. As a result, the sound absorption material 10 formed when the conductor 11 is exposed at the upper and lower parts can be obtained. The obtained sound absorption material 10 may be used as the above-mentioned sound absorption unit 120.

As is apparent from the above description, the ultrasonic probe apparatus and the ultrasonic imaging apparatus according to the embodiments can efficiently absorb ultrasonic waves emitted in the direction from the ultrasonic elements to the ultrasonic probe, resulting in implementation of improved acoustic throughput.

According to the ultrasonic probe apparatus and the ultrasonic imaging apparatus, a processor of the ultrasonic probe apparatus can be connected to a main body thereof without exposing the conductive lines to the outside, so that product durability, such as mechanical stability, electrical deterioration, corrosiveness, and heat-resistance, can be improved, resulting in increased product reliability.

According to the ultrasonic probe apparatus and the ultrasonic imaging apparatus, the accuracy of impedance matching of signal lines of a low volume dissemination system of semiconductors and a time error between two signals needed for constructing one pair of patterns, resulting in reduction of signal loss.

According to the ultrasonic probe apparatus and the ultrasonic imaging apparatus, heat generated from the processor contained in the ultrasonic probe and a substrate on which the processor is disposed can be easily and quickly emitted to the outside.

According to the ultrasonic probe apparatus and the ultrasonic imaging apparatus, the ultrasonic probe is reduced in weight, resulting in greater convenience.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An ultrasonic probe apparatus comprising:

an ultrasonic transducer configured to output an electrical signal upon receiving ultrasonic waves;

a sound absorption unit, one surface of which is an installation surface of the ultrasonic transducer, and being electrically connected to the ultrasonic transducer;

a first electronic circuit electrically connected to the sound absorption unit; and a second electronic circuit disposed between the sound absorption unit and the first electronic circuit, configured to electrically interconnect the first electronic circuit and the sound absorption unit, wherein one surface of the second electronic circuit faces another surface of the sound absorption unit, and another surface of the second electronic circuit faces one surface of the first electronic circuit

*wherein the sound absorption unit includes at least one first connection unit electrically connected to the ultrasonic transducer,*

*wherein the second electronic circuit includes:*

*a first substrate connection unit provided to pass through from the one surface of the second electronic circuit to the another surface of the second electronic circuit, connected to the at least one first connection unit and configured to electrically connect the sound absorption unit and the first electronic circuit; and*

*a second substrate connection unit provided at a position not in contact with the at least one first connection unit of the sound absorption unit and configured to electrically connect the first electronic circuit and an output unit of the second electronic circuit.*

[2. The ultrasonic probe apparatus according to claim 1, wherein the second electronic circuit includes a substrate connection unit electrically connected to the first electronic circuit.]

[3. The ultrasonic probe apparatus according to claim 2, wherein the substrate connection unit includes a first substrate connection unit configured to electrically interconnect the sound absorption unit and the first electronic circuit.]

[4. The ultrasonic probe apparatus according to claim 3, wherein the first substrate connection unit is electrically connected to the ultrasonic transducer.]

[5. The ultrasonic probe apparatus according to claim 4, wherein the sound absorption unit includes at least one first connection unit electrically connected to the ultrasonic transducer, wherein the first substrate connection unit contacts the first connection unit.]

6. The ultrasonic probe apparatus according to claim [2] *1*, wherein the [second electronic circuit includes at least one] output unit *is* configured to output a signal processed by the first electronic circuit[, wherein the substrate connection unit includes a second substrate connection unit configured to electrically interconnect the first electronic circuit and the at least one output unit].

7. The ultrasonic probe apparatus according to claim [2] *1*, wherein the *first* substrate connection unit [includes] *and the second substrate connection unit include*:

a first opening configured to pass through a range from the one surface to the another surface of the second electronic circuit; and a conductor installed at an inner lateral surface of the first opening and electrically coupled to the first electronic circuit.

8. The ultrasonic probe apparatus according to claim 7, wherein the conductor is configured to shield the first opening.

9. The ultrasonic probe apparatus according to claim 7, wherein the *first* substrate connection unit *and the second substrate connection unit* further [includes] *include* a second opening formed to pass through the conductor.

10. The ultrasonic probe apparatus according to claim 9, wherein the *first* substrate connection unit *and the second substrate connection unit* further [includes] *include* a filling material configured to shield the second opening.

11. The ultrasonic probe apparatus according to claim 7, wherein the conductor is deposited on the inner lateral surface of the first opening.

12. The ultrasonic probe apparatus according to claim 7, wherein the conductor is installed at the one surface of the second electronic circuit located in a vicinity of the first opening.

13. The ultrasonic probe apparatus according to claim 1, wherein the second electronic circuit includes a rigid flexible printed circuit board (PCB).

14. The ultrasonic probe apparatus according to claim 13, wherein the second electronic circuit includes at least one of a first region that is not curved and a second region that is flexibly curved.

15. The ultrasonic probe apparatus according to claim 14, wherein [the second electronic circuit includes a substrate connection unit that is electrically connected to the first electronic circuit and is] *the first substrate connection unit and the second substrate connection unit are* formed in the first region.

16. The ultrasonic probe apparatus according to claim [2] *1*, wherein:

a second connection unit is mounted [to] *on* the first electronic circuit *and includes a third connection unit and a fourth connection unit*, the [second] *third* connection unit being attached to the *first* substrate connection unit of the second electronic circuit *and the fourth connection unit, being attached to the second substrate connection unit, of the second electronic circuit*.

17. The ultrasonic probe apparatus according to claim 16, further comprising:

a separation unit disposed between the second electronic circuit and the first electronic circuit, and formed of a nonconductive material that prevents the second electronic circuit from directly contacting the first electronic circuit.

18. The ultrasonic probe apparatus according to claim 17, wherein the second connection unit [is mounted to the first electronic circuit so as to pass] *passes* through the separation unit.

19. The ultrasonic probe apparatus according to claim 1, further comprising:

a heat conduction unit mounted to another surface of the first electronic circuit, and to perform heat transmission of the first electronic circuit.

20. The ultrasonic probe apparatus according to claim 1, wherein the sound absorption unit includes:

a sound absorption material for absorbing sound; and

[a first] *the at least one first* connection unit configured to pass through the sound absorption material so as to electrically interconnect the ultrasonic transducer and the first electronic circuit.

21. The ultrasonic probe apparatus according to claim 20, wherein *the* at least one first connection unit is mounted to a single ultrasonic transducer.

[22. The ultrasonic probe apparatus according to claim 1, further comprising:

an acoustic enhancer disposed between the ultrasonic transducer and the sound absorption unit, and configured to amplify the electrical signal generated from the ultrasonic transducer.]

23. The ultrasonic probe apparatus according to claim 1, wherein the sound absorption unit is formed of a sound absorption material configured to absorb sound waves or ultrasonic waves.

[24. The ultrasonic probe apparatus according to claim 1, wherein:

a seating surface at which the ultrasonic transducer or an acoustic enhancer is seated is formed at the one surface of the sound absorption unit, wherein the acoustic enhancer is coupled to the ultrasonic transducer so as to amplify the electrical signal generated from the ultrasonic transducer.]

25. The ultrasonic probe apparatus according to claim 1, wherein the first electronic circuit includes a processor configured to focus signals generated from the ultrasonic transducer.

26. The ultrasonic probe apparatus according to claim 1, wherein the first electronic circuit includes at least one application specific integrated circuit (ASIC).

27. An ultrasonic imaging apparatus comprising:

an ultrasonic probe configured to receive ultrasonic waves; and a main body configured to control operations of the ultrasonic probe, and to perform image processing of an ultrasound image corresponding to the received ultrasonic waves, wherein the ultrasonic probe includes:

an ultrasonic transducer configured to output an electrical signal upon receiving the ultrasonic waves;

a sound absorption unit, one surface of which is an installation surface of the ultrasonic transducer and is electrically connected to the ultrasonic transducer;

a first electronic circuit electrically connected to the sound absorption unit; and a second electronic circuit disposed between the sound absorption unit and the first electronic circuit, configured to electrically interconnect the first electronic circuit and the sound absorption unit, wherein one surface of the second electronic circuit faces another surface of the sound absorption unit, and another surface of the second electronic circuit faces one surface of the first electronic circuit

*wherein the sound absorption unit includes at least one first connection unit electrically connected to the ultrasonic transducer,*

*wherein the second electronic circuit includes:*

*a first substrate connection unit provided to pass through from the one surface of the second electronic circuit to the another surface of the second electronic circuit, connected to the at least one first connection unit, and configured to electrically connect the sound absorption unit and the first electronic circuit; and*

*a second substrate connection unit provided a position not in contact with the at least one first connection unit of the sound absorption unit, and configured to electrically connect the first electronic circuit and an output unit of the second electronic circuit.*

[28. The ultrasonic imaging apparatus according to claim 27, wherein the second electronic circuit includes a substrate connection unit electrically connected to the first electronic circuit.]

[29. The ultrasonic imaging apparatus according to claim 28, wherein the substrate connection unit includes a first substrate connection unit configured to electrically interconnect the sound absorption unit and the first electronic circuit.]

[30. The ultrasonic imaging apparatus according to claim 29, wherein the first substrate connection unit is electrically connected to the ultrasonic transducer.]

[31. The ultrasonic imaging apparatus according to claim 30, wherein the sound absorption unit includes at least one first connection unit electrically connected to the ultrasonic transducer, wherein the first substrate connection unit contacts the first connection unit.]

32. The ultrasonic imaging apparatus according to claim [28] *27*, wherein the [second electronic circuit includes at least one] output unit *is* configured to output a signal processed by the first electronic circuit[, wherein the substrate connection unit includes a second substrate connection unit configured to electrically interconnect the first electronic circuit and the at least one output unit].

33. The ultrasonic imaging apparatus according to claim 27, wherein the second electronic circuit includes a rigid flexible printed circuit board (PCB).

34. The ultrasonic imaging apparatus according to claim 33, wherein the second electronic circuit includes at least one of a first region that is not curved and a second region that is flexibly curved.

35. The ultrasonic imaging apparatus according to claim 34, wherein [the second electronic circuit includes a substrate connection unit that is electrically connected to the first electronic circuit and is] *the first substrate connection unit and the second substrate connection unit are* formed in the first region.

36. The ultrasonic imaging apparatus according to claim [29] *27*, wherein: a second connection unit is mounted [to] *on* the first electronic circuit *and includes a third connection unit and a fourth connection unit*, the [second] *third* connection unit being attached to the *first* substrate connection unit of the second electronic circuit *and the fourth connection unit being attached to the second substrate connection unit of the second electronic circuit*.

37. The ultrasonic imaging apparatus according to claim 36, further comprising:

a separation unit disposed between the second electronic circuit and the first electronic circuit, and formed of a nonconductive material that prevents the second electronic circuit from directly contacting the first electronic circuit.

38. The ultrasonic imaging apparatus according to claim 37, wherein the second connection unit [is mounted to the first electronic circuit so as to pass] *passes* through the separation unit.

39. The ultrasonic imaging apparatus according to claim 27, further comprising:

a heat conduction unit mounted to another surface of the first electronic circuit, and to perform heat transmission of the first electronic circuit.

40. The ultrasonic imaging apparatus according to claim 27, wherein the sound absorption unit includes:

a sound absorption material for absorbing sound; and

[a first] *the at least one first* connection unit configured to pass through the sound absorption material so as to electrically interconnect the ultrasonic transducer and the first electronic circuit.

41. The ultrasonic imaging apparatus according to claim 40, wherein *the* at least one first connection unit is mounted to a single ultrasonic transducer.

[42. The ultrasonic imaging apparatus according to claim 27, further comprising:

an acoustic enhancer disposed between the ultrasonic transducer and the sound absorption unit, and configured to amplify the electrical signal generated from the ultrasonic transducer.]

43. The ultrasonic imaging apparatus according to claim 27, wherein the sound absorption unit is formed of a sound absorption material configured to absorb sound waves or ultrasonic waves.

[44. The ultrasonic imaging apparatus according to claim 27, wherein:

a seating surface at which the ultrasonic transducer or an acoustic enhancer is seated is formed at the one surface of the sound absorption unit, wherein the acoustic enhancer is coupled to the ultrasonic transducer so as to amplify the electrical signal generated from the ultrasonic transducer.]

45. The ultrasonic imaging apparatus according to claim 27, wherein the first electronic circuit includes a processor configured to focus signals generated from the ultrasonic transducer.

46. The ultrasonic imaging apparatus according to claim 27, wherein the first electronic circuit includes at least one application specific integrated circuit (ASIC).

* * * * *